(12) United States Patent
Wallace et al.

(10) Patent No.: US 6,669,719 B2
(45) Date of Patent: Dec. 30, 2003

(54) INTRACRANIAL STENT AND METHOD OF USE

(75) Inventors: George Wallace, San Clemente, CA (US); Jay Lenker, San Clemente, CA (US); Thomas J. Berryman, San Clemente, CA (US); Robert R. Greene, San Clemente, CA (US); Rodney Brenneman, San Clemente, CA (US)

(73) Assignee: MicroTherapeutics, Inc., Irvine, CA (US)

( * ) Notice: Subject to any disclaimer, the term of this patent is extended or adjusted under 35 U.S.C. 154(b) by 0 days.

(21) Appl. No.: 09/897,218

(22) Filed: Jul. 2, 2001

(65) Prior Publication Data

US 2002/0004676 A1 Jan. 10, 2002

Related U.S. Application Data

(63) Continuation of application No. 08/762,110, filed on Dec. 9, 1996, now Pat. No. 6,254,628.

(51) Int. Cl.$^7$ ................................................. A61F 2/06
(52) U.S. Cl. ....................... 623/1.12; 606/108
(58) Field of Search ............................. 623/1.12, 1.15, 623/1.2, 1.11, 1.23; 606/108

(56) References Cited

U.S. PATENT DOCUMENTS

| | | | |
|---|---|---|---|
| 4,665,918 A | 5/1987 | Garza et al. ................. | 623/1 X |
| 4,732,152 A | 3/1988 | Wallsten et al. ............. | 623/1 X |
| 4,738,666 A | 4/1988 | Fuqua ......................... | 604/280 |
| 4,740,207 A | 4/1988 | Kreamer ...................... | 623/1 |

(List continued on next page.)

FOREIGN PATENT DOCUMENTS

| | | | |
|---|---|---|---|
| EP | 0709067 A2 | 1/1996 | ............. A61F/2/06 |
| WO | WO 93/17636 | 9/1993 | |
| WO | 9404096 | 3/1994 | |
| WO | 9421196 | 9/1994 | |

OTHER PUBLICATIONS

Palmaz, Intravascular Stenting, 15 Cardiovasc. Interv. Rad. 279 (1992).
Palmaz, *Intravascular Stents: Tissue–Stent Interactions and Design Considerations*, 160 Am. J. Rad. 613 (Mar. 1993).
Zollikofer, Historical Overview On The Development And Characteristics Of Stents And Future Outlooks, 15 Cardiovasc. Intervent. Radiol. 272 (1992).
Berry, et al., *A Method To Evaluate The Elastic Behavior Of Vascular Stents*, 7 J Vasc. Interv. Radiol. 381–5 (May–Jun. 1996).
Abbott, et al., *Effect Of Compliance Mismatch On Vascular Graft Patency*, 5 J. Vasc. Surg. 376 (1987).
Palmaz, *Intravascular Stents: Tissue–Stent Interactions and Design Considerations*, 160 Am. J. Rad. 613 (Mar. 1993).
Civit, et al., Aneurysm Clipping After Endovascular Treatment With Coils, 38 Neurosurgery 955 (May 1996).
Wakhloo, et al., Self-Expanding Nitinol Stents in Canine Vertebral Arteries, 16 AJNR 1043 (May 1995).

(List continued on next page.)

Primary Examiner—Michael H. Thaler
(74) Attorney, Agent, or Firm—K. David Crockett, Esq.; Crockett & Crockett

(57) ABSTRACT

A stent and stent catheter for intra-cranial use. The stent is a rolled sheet stent and is releasably mounted on the distal tip of the catheter by means of a non-sliding retention and release mechanism. The non-sliding release mechanism is operated remotely at the proximal end of the catheter by means of a linear translator. The stent is rolled tightly on the distal tip of the catheter and flexibility of the tightly rolled stent is promoted by ribbed or slatted construction (or, alternatively, slotted construction) in which the various layers of the stent are provided with numerous slats which counter align when the stent is expanded to form an imperforate wall from a plurality of perforate layers.

3 Claims, 27 Drawing Sheets

U.S. PATENT DOCUMENTS

| | | | |
|---|---|---|---|
| 4,776,337 A | 10/1988 | Palmaz | 606/194 |
| 4,830,003 A | 5/1989 | Wolff et al. | 128/343 |
| 4,878,906 A | 11/1989 | Lindemann et al. | 623/1 |
| 4,923,464 A | 5/1990 | DiPisa | 606/195 |
| 4,969,890 A | 11/1990 | Sugita et al. | 606/192 |
| 5,007,926 A | 4/1991 | Derbyshire | 623/1 |
| 5,026,377 A | 6/1991 | Burton et al. | 606/108 |
| 5,100,429 A | 3/1992 | Sinofsky et al. | 606/195 |
| 5,139,480 A | 8/1992 | Hickle et al. | 606/191 |
| 5,147,370 A | 9/1992 | McNamara et al. | 606/108 |
| 5,211,654 A | 5/1993 | Kaltenbach | 606/191 |
| 5,306,294 A | 4/1994 | Winston | 623/1 |
| 5,354,309 A | 10/1994 | Schnepp-Pesch et al. | 606/198 |
| 5,372,600 A | 12/1994 | Beyar et al. | 606/108 |
| 5,405,379 A | 4/1995 | Lane | 623/1 |
| 5,411,549 A | 5/1995 | Peters | 606/194 |
| 5,441,515 A | 8/1995 | Khosravi | 606/194 |
| 5,443,458 A | 8/1995 | Eury | 606/198 |
| 5,443,500 A | 8/1995 | Sigwart | 623/1 |
| 5,449,373 A | 9/1995 | Pinchasik et al. | 606/198 |
| 5,545,210 A | 8/1996 | Hess | 623/1 |
| 5,562,603 A | 10/1996 | Moll et al. | 600/204 |
| 5,603,722 A | 2/1997 | Phan | 623/1 |
| 5,637,113 A | 6/1997 | Tartaglia et al. | 623/1 |

OTHER PUBLICATIONS

Geremia, at al, Embolization of Experimentally Created aneurysms with Intravascular Stent devices, 15 AJNR 1223 (Aug. 1994).

Hull, The Wallstent In Peripheral Vascular Disease: For Iliac Use Only, 6 JVIR 841 (Nov.–Dec. 1995).

Szikora, et al., Combined Use Of Stents And Coils To Treat Experimental Wide–Necked Carotid Aneurysms, 15 AJNR 1091 (Jun. 1994).

Marks, et al., Stent Placement for Arterial and Venous Cerebrovascular Disease, 191 Radiology 441 (1994).

Eskridge, Neurovascular Stents, 191 Radiology 313 (1994).

Becker, Should Metallic intravascular Stents Be Used to Treat Cerebrovascular Occlusive Diseases, 191 Radiology 309 (1994).

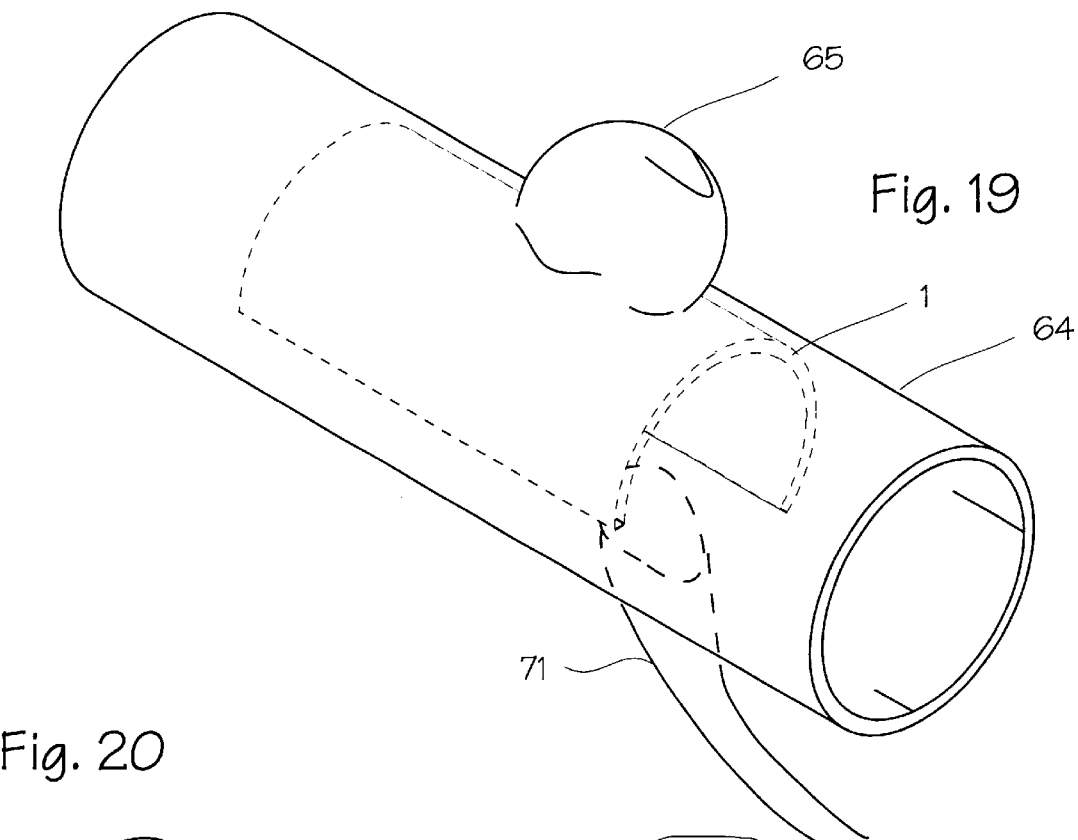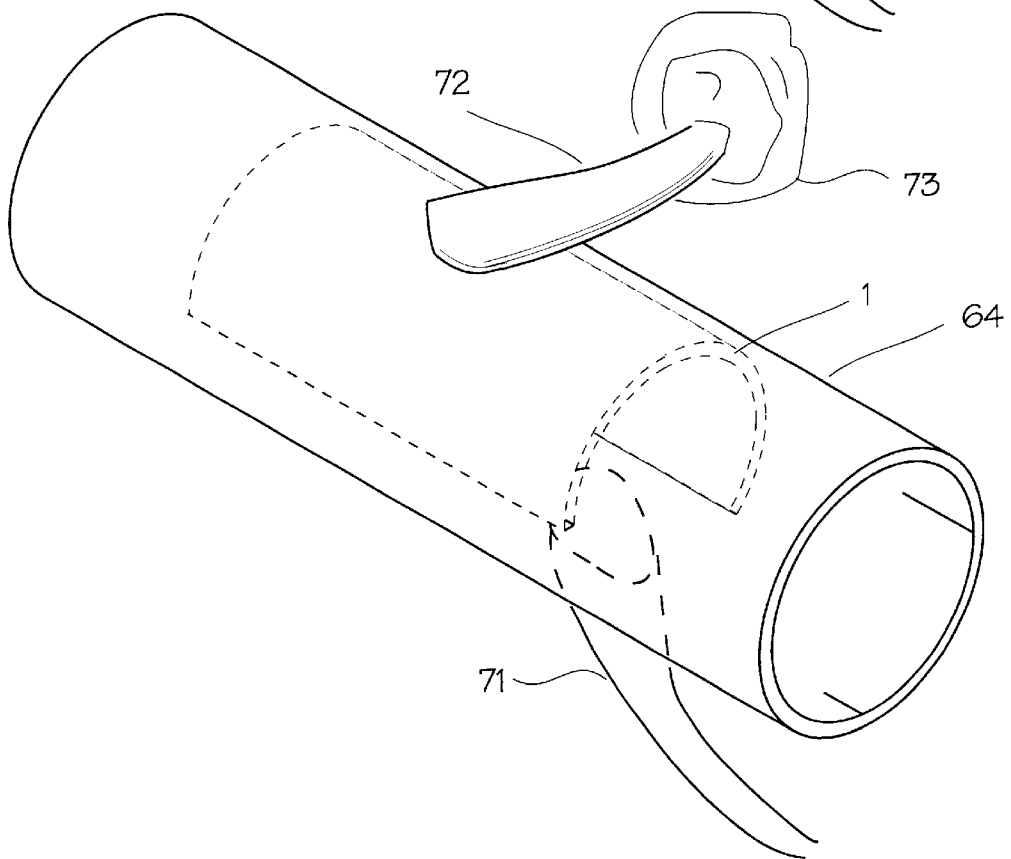

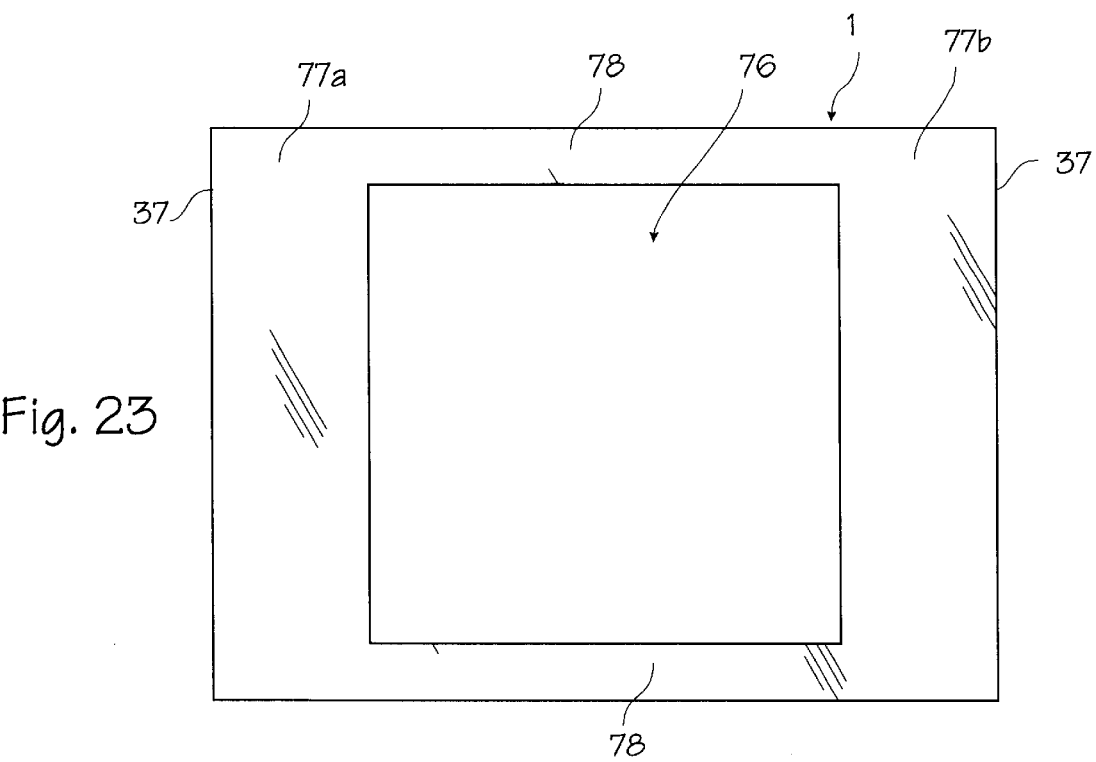
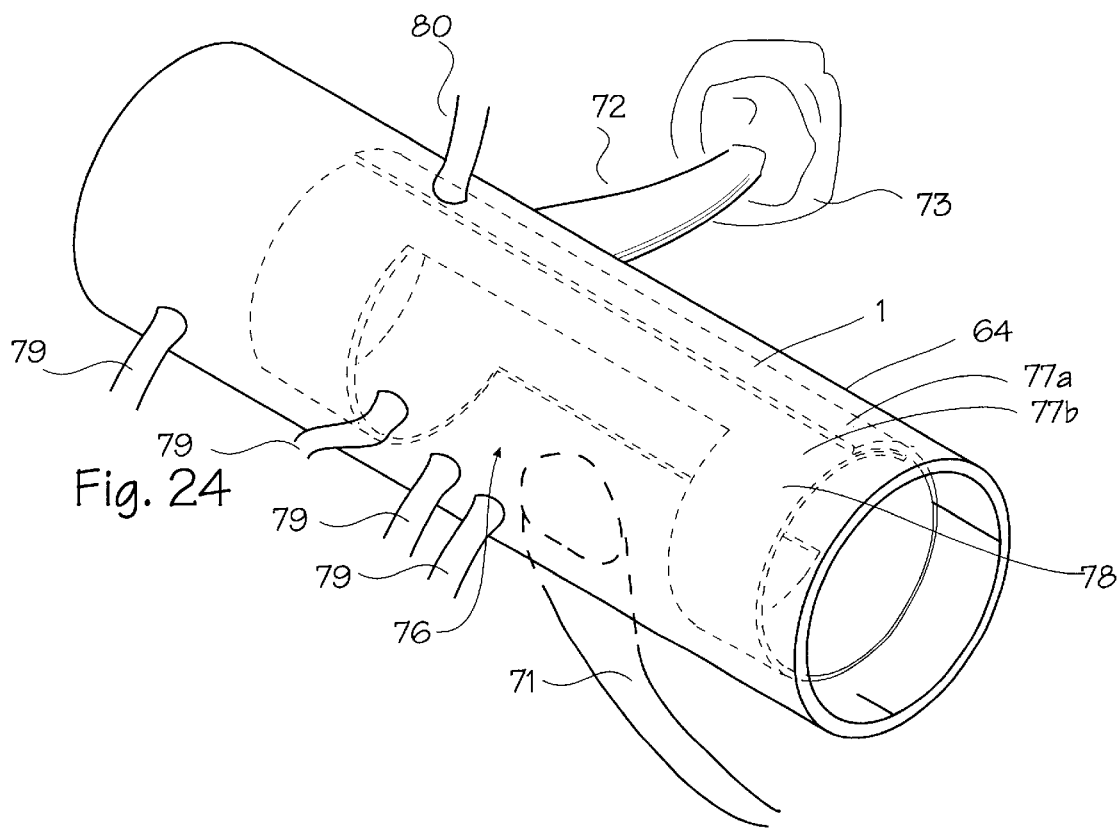

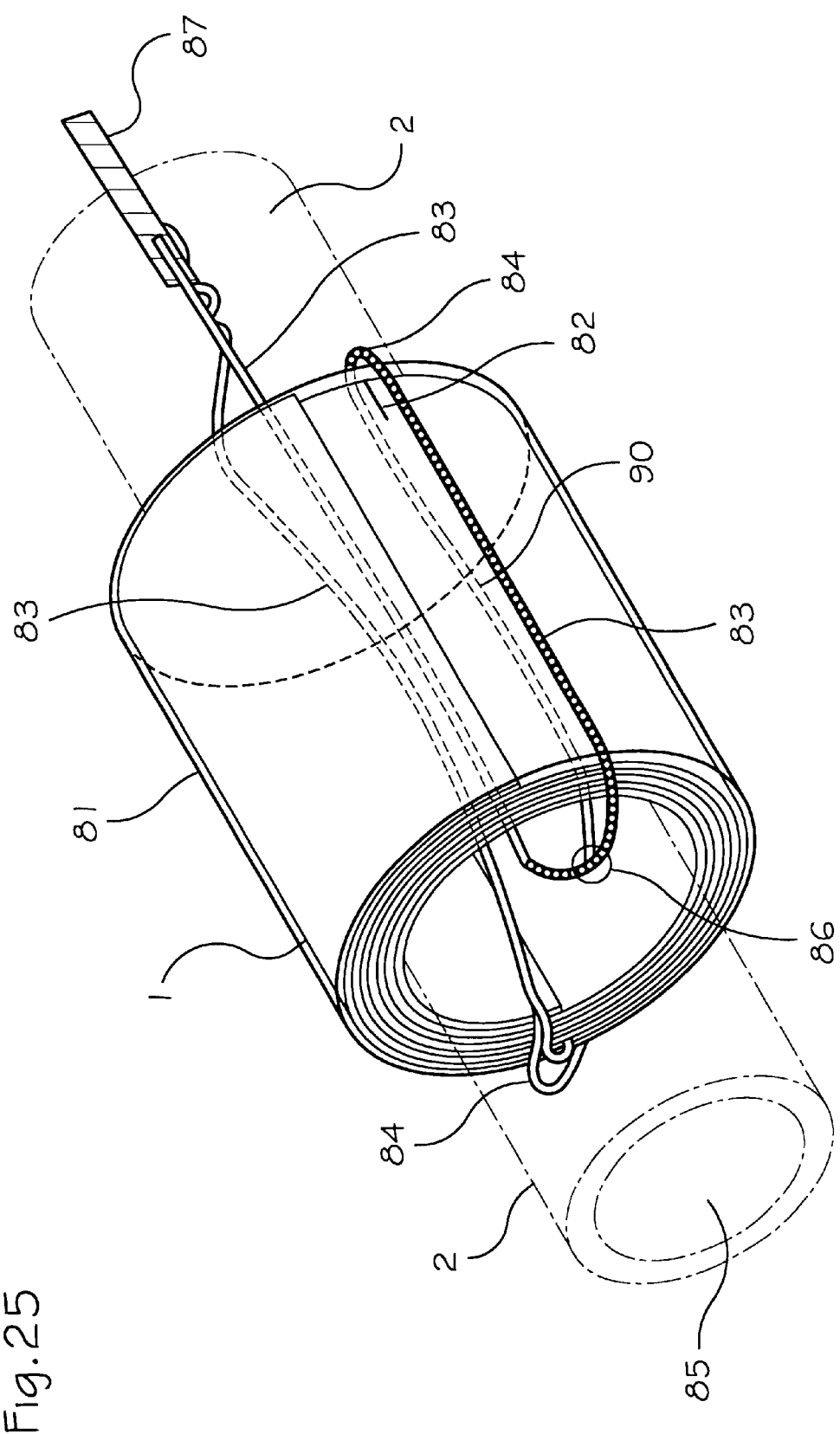

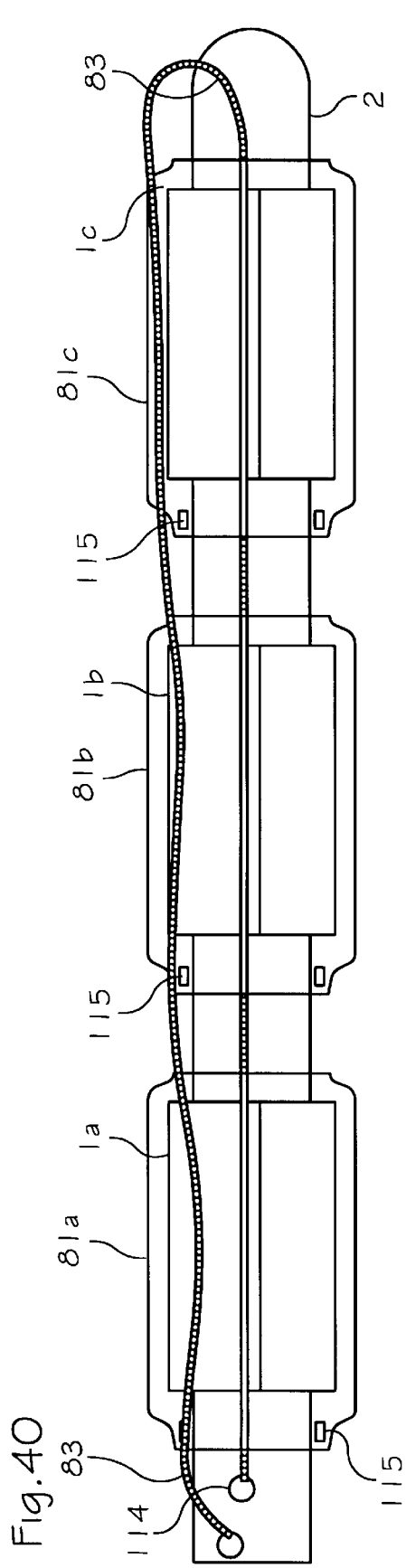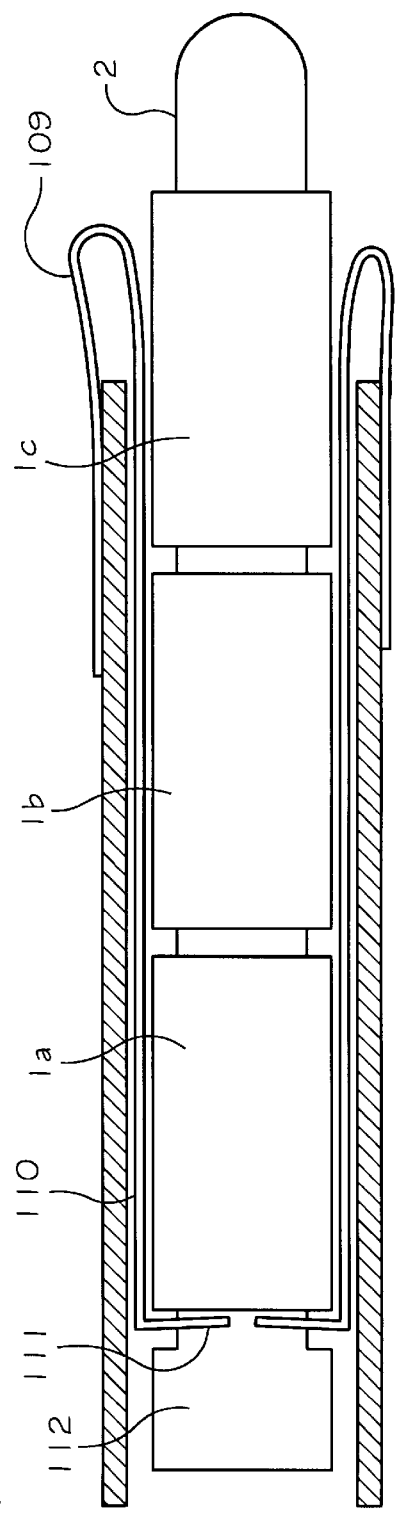

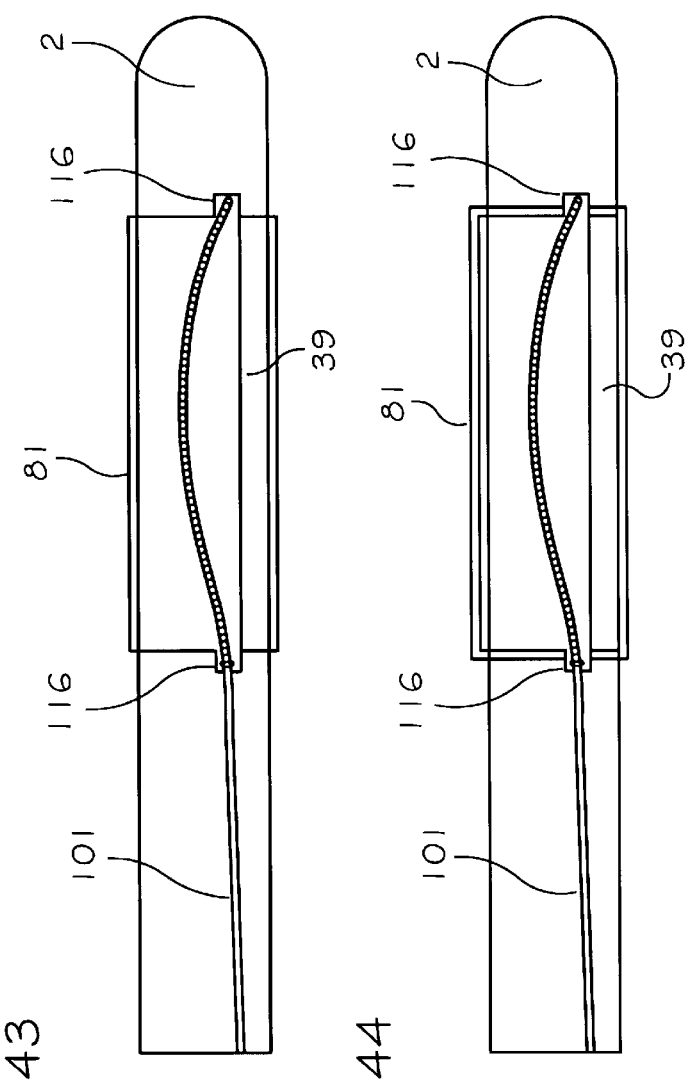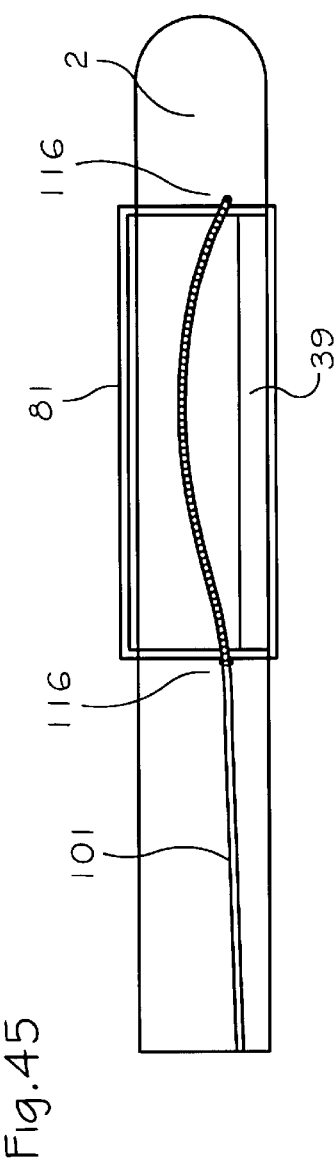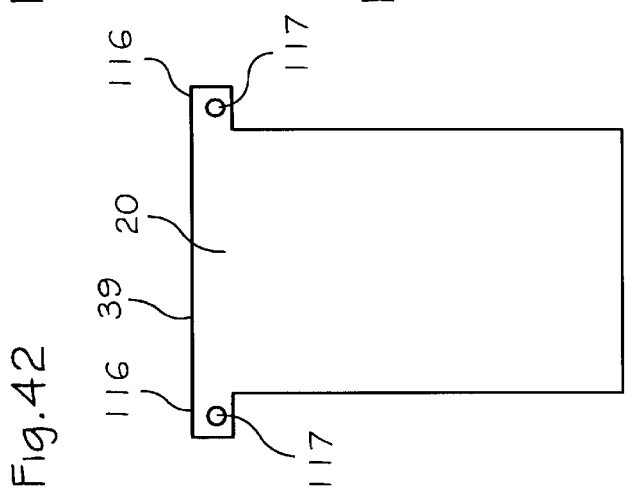

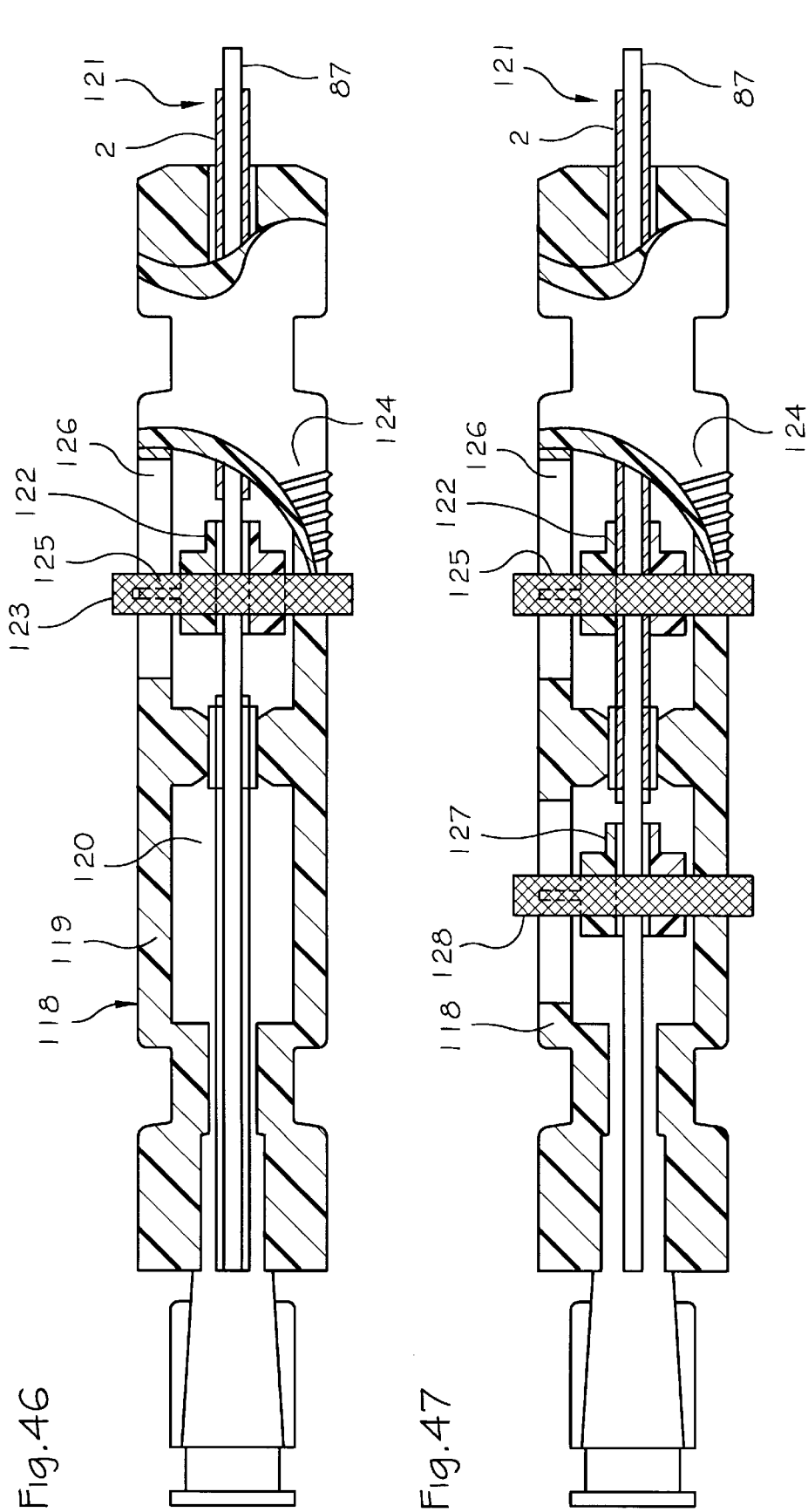

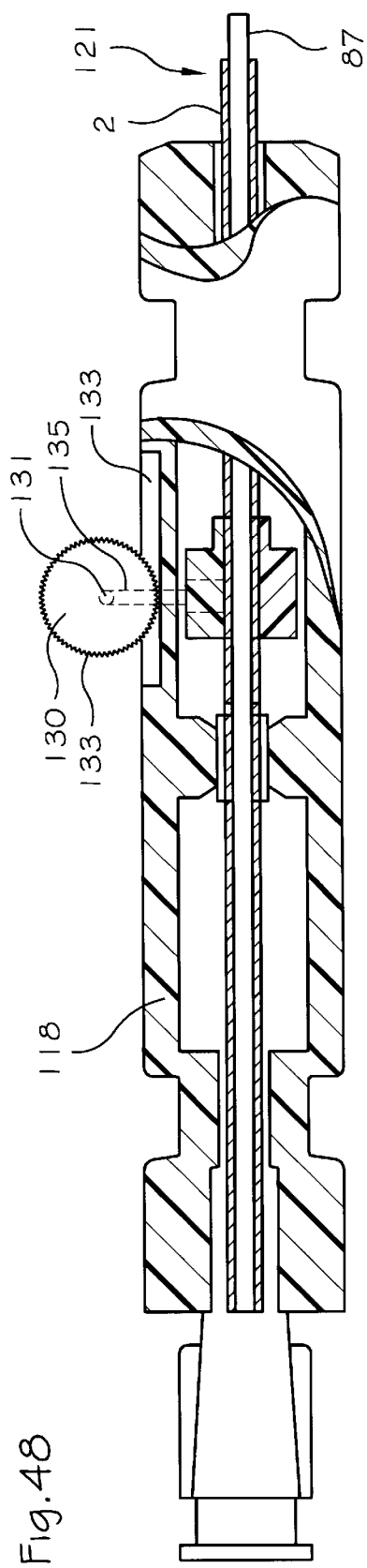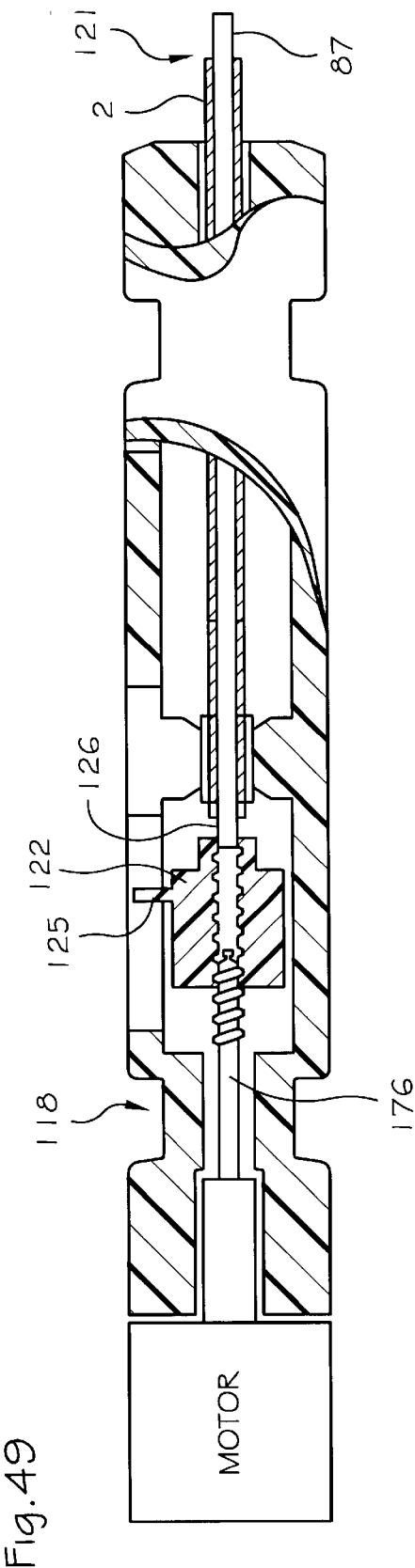
Fig.48
Fig.49

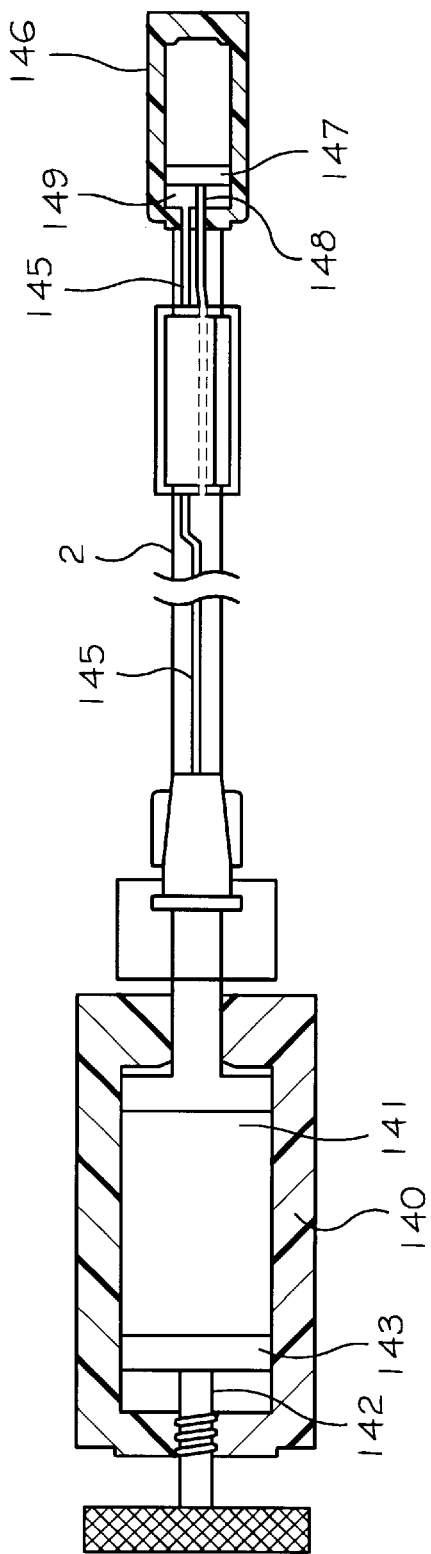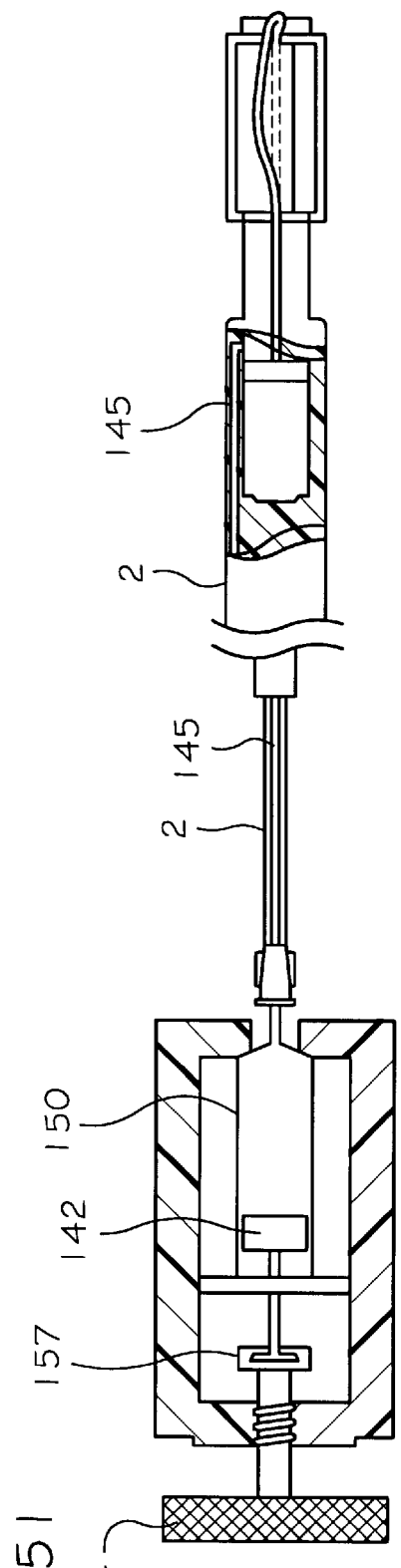

INTRACRANIAL STENT AND METHOD OF USE

This application is a continuation application of U.S. patent application Ser. No. 08/762,110, filed Dec. 9, 1996, now U.S. Pat. No. 6,254,628.

FIELD OF THE INVENTION

This invention relates to disease delivery systems for stents to be used to treat vascular disease.

BACKGROUND OF THE INVENTION

The inventions described below were developed with the goal of providing new and better therapies for certain types of vascular disease for which the present day therapies are widely regarded as inadequate. Vascular disease includes aneurysms which can rupture and cause hemorrhage, atherosclerosis which can cause the occlusion of the blood vessels, vascular malformation and tumors. Occlusion of the coronary arteries, for example, is a common cause of heart attack. Vessel occlusion or rupture of an aneurysm within the brain are causes of stroke. Tumors fed by intra-cranial arteries can grow within the brain to the point where they cause a mass effect. The mass and size of the tumor can cause a stroke or the symptoms of stroke, requiring surgery for removal of the tumor or other remedial intervention.

Other therapies for occlusions of various arteries are under development. Balloon angioplasty is a technique in which a balloon is inserted into a stenosis which occludes or partially occludes an artery and is inflated in order to open the artery. Atherectomy is a technique in which occlusive atheromas are cut from the inner surface of the arteries. The newly preferred therapy for coronary occlusions is placement of an expanded metal wire-frame, called a stent, within the occluded region of the blood vessel to hold it open. Stents of various construction have been proposed, including the Palmaz-Schatz™ balloon expandable metal stent, the Wallstent self-expanding braided metal stent, the Strecker knitted metal stent, the Instent™ coil stent, the Cragg coiled stent and the Gianturco Z stent. Stents have been proposed for treatment of atherosclerosis in the neck, but carotid endarterectomy is still the preferred treatment for stenosis. Most perioperative strokes are thought to be caused by technical errors during endarterectomy (see Becker, Should Metallic Vascular Stents Be Used To Treat Cerebrovascular Occlusive Disease, 191 Radiology 309 (1994)). The same concerns militate against other forms of therapy such as angioplasty for treatment of the carotid arteries. Various factors, including poor long-term patency, distal emboli causing a stroke, the potential for crushing from external pressure, and the need for long term anti-coagulation, lead to the avoidance of certain stents in vessels smaller than the iliac arteries or in locations susceptible to external pressure. See, for example, Hull, The Wallstent in Peripheral Vascular Disease, For Iliac Use Only, 6 JVIR 884 (November.–December 1995).

Stent-grafts have been proposed and used to treat aneurysms in the large blood vessels such as the aorta, and these typically include tube graft material supported by a metallic stent. These stent-grafts are designed for use in the large blood vessels, and the various layers of stents and grafts make them unsuitable for use in smaller blood vessels. Stent-grafts are not currently used in the coronary arteries which are typically 3 or 4 mm in internal diameter. Rolled stents have been proposed for use in aortic aneurysms. For example, Lane, Self Expanding Vascular Endoprosthesis for Aneurysms, U.S. Pat. No. 5,405,379 (Apr. 11, 1995) suggests the use of a polypropylene sheet placed in the abdominal or thoracic aorta to bridge aneurysms. It is particularly emphasized in Lane that the rolled sheet must be imperforate. Winston, Stent Construction of Rolled Configuration, U.S. Pat. No. 5,306,294 (Apr. 26, 1994) proposes a rolled sheet of stainless steel. Neither device has been approved for use in humans. The Winston device has not been used in humans. Of similar construction are the single layer rolled stents such as Kreamer, Intraluminal Graft, U.S. Pat. No. 4,740,207 (Apr. 26, 1988) and its reissue Re 34,327 (Jul. 27, 1993), which are expanded by balloon and include a ratchet mechanism which projects into the lumen of the stent, thus making it unsuitable for critical vessels in the brain and small diameter vessels. Khosravi, Ratcheting Stent, U.S. Pat. No. 5,441,155 (Aug. 15, 1995) and Sigwart, Intravascular Stent, U.S. Pat. No. 5,443,500 (Aug. 22, 1995) are other examples of rolled stents with ratcheting locking mechanisms.

Aneurysms of peripheral arteries and arteries of the neck have been treated experimentally with open walled stents such as the Strecker braided stent. Szikora, et al., Combined use of Stents and Coils to treat Experimental Wide-Necked Carotid Aneurysms, 15 AJNR 1091 (June 1994) illustrates use of a Strecker stent in the proximal vertebral arteries in dogs, and teaches that an open walled or porous stent is required to avoid excessive ingrowth. The Strecker stent has a small metal to blood vessel surface ratio, and has large openings between each of the wires making up the stent. The current technique in the use of open walled stents in the aneurysms of peripheral arteries is based on the theory that placement of the open walled stent slows the blood flow in the aneursymal sac, leading eventually to the formation of clots and fibrous masses which occlude the aneurysm. This technique has been combined with placement of micro-coils through the wall of the stent and into the aneurysm to further encourage fibrous tissue development within the aneurysm. The Szikora article and others show that knitted stents have not been effective in isolating an aneurysm from the circulatory system. Another problem noted with this technique is that blood clots can escape the open walled stent.

Stents have not previously been used for aneurysms of the blood vessels in the brain. The vessels in the brain likely to develop stenosis, aneurysms, AVM's and side branches requiring occlusion have diameters of about 1 mm to 5 mm, and can be accessed only via highly tortuous routes through the vascular system. Instead, surgical clipping, resection, complete occlusion with acrylic-based adhesives (super glue) or small balloons (thereby intentionally occluding the downstream portion of the blood vessel and any portion of the brain supplied by that portion), stuffing with foreign objects, etc. have been used. In a method of current interest, small coils are stuffed into the aneurysm via a catheter. One such small coil is known as the Guglielmi Detachable Coil or GDC. After placement of a few coils, which partially obstruct blood flow in the aneurysm, the blood clots or fibrous matter forms within the sac. This technique has reportedly resulted in clots and coils falling out of the sac, and the technique is not used on wide-neck aneurysms. Aneurysm clipping, in which the skull is opened and the brain dissected to expose the outside of the aneurysm, followed by placement of clips at the base of the aneurysm, is also an option for treatment. However, these techniques do not always effect an immediate and complete seal of the aneurysm from the high pressure of the circulatory system, and rupture, leakage and deadly complications occur. Aneurysm rupture and bleeding during surgical clipping and shortly after the clip placement is a significant problem and add difficulty to the procedure. Examples of the problems inherent in the use of both GDC's and aneurysm clips are illustrated in Civit, et al., Aneurysm Clipping After Endovascular Treatment With Coils, 38 Neurosurgery 955 (May 1996) which reports that several patients in the study died after unsuccessful coil placement and before they could be re-treated with the open skull clip placement. Thus the article illustrates that GDC's do not always work, and when they fail they may leave the patient in a critical condition. As illustrated in the article, bleeding during surgical clipping and shortly after the clip placement is also a frequent problem.

From experiences like this, it is apparent that the ultimate goal of intracranial aneurysm treatment is the complete or nearly complete exclusion of the aneurysm cavity from the circulation, which prevents bleeding into the brain cavity and prevents formation of distal blood clots. This goal may be achieved immediately to ensure successful treatment by means of a substantially imperforate stent. It may also be achieved with a slightly perforated stent which alters flow in such a way that compete clotting, over time, is initiated within the aneurysm. It may also be achieved with a perforate stent through which embolic material such as coils are placed in the aneurysm. The treatments may be accomplished by placement of the stents described below which generally do not require the use of balloons for expansion of the stent, so that the blood vessel being treated is not occluded during placement of the stent.

Typically, the stents described below will be delivered percutaneously, introduced into the body through the femoral artery, steered upwardly through the aorta, vena cava, carotid or vertebral artery, and into the various blood vessels of the brain. Further insertion into the brain requires passage through the highly tortuous and small diameter intra-cranial blood vessels. The Circle of Willis, a network of blood vessels which is central to the intracranial vascular system, is characterized by numerous small arteries and bends. Passage of a stent from the internal carotid through the Circle of Willis and into the anterior cerebral artery (for example) requires a turn of about 60° through blood vessels of only 1–5 mm in diameter. Clinically, many significant aneurysms take place in the Circle of Willis and approaching blood vessels. The stent and delivery systems described herein are intended for use in such highly tortuous vessels, particularly in the Circle of Willis, the vertebral and carotid siphons and other major blood vessels of the brain. At times, pathologically tortuous vessels may be encountered in the deeper vessels of the brain, and these vessels may be characterized by small diameter, by branching at angles in excess of 90° and by inaccessibility with guide wires larger than the standard 0.018 guide-wires. These pathologically tortuous vessels may also be subject to aneurysms and AVM's which can be treated with the stents and delivery systems described below.

Various inventors have proposed systems for delivering stents into the larger less tortuous vasculature of the abdomen, chest, arms and legs. Garza, Prosthesis System and Method, U.S. Pat. No. 4,665,918 (1987), describes a delivery system for a stent designed to open an occlusion in a blood vessel. The stent is rolled on a catheter, and the catheter is covered with a sheath that fits closely over the catheter. The stent is held in place on the catheter by the sheath, and is released by pulling the sheath backward (proximally) to uncover the stent.

Winston, Stent Construction of Rolled Configuration, U.S. Pat. No. 5,306,294 (Apr. 26, 1994) shows a rolled sheet stent intended for use in bridging aneurysms and opening occluded blood vessels. The stent is self expanding, and does not require a balloon to force it to unwind to a diameter large enough to engage the aorta with enough force to hold it in place. The delivery system shown in Winston includes a rolled stent rolled upon a spool which in turn is mounted on the distal tip of a delivery catheter. The assembly is housed within the lumen in the distal tip of a guide catheter. Control wires shown in Winston may be used to hold the stent in the tightly wound state, and may be pulled proximally to release the stent.

Lane, Self Expanding Vascular Endoprosthesis for Aneurysms, U.S. Pat. No. 5,405,379 (Apr. 11, 1995) shows a rolled sheet stent intended for use in bridging abdominal aneurysms. The stent is self expanding, and does not require a balloon to force it to unwind to a diameter large enough to engage the aorta with enough force to hold it in place. The delivery system shown in Lane includes a rolled stent inside the lumen in the distal tip of a delivery catheter, and a push rod located behind the stent. The stent is deployed when the push rod is used to push the stent distally out the end of the delivery catheter as the delivery catheter is pulled proximally to uncover the stent and allow it to unwind.

Kreamer, Intraluminal Graft, U.S. Pat. No. 4,740,207 (Apr. 26, 1988) shows a tube stent, comprising a solid walled tube with ratcheting tongue and groove mechanism. The stent is mounted on an angioplasty balloon and expanded to size within an artery by force of the balloon. Likewise, Sigwart, Intravascular Stent, U.S. Pat. No. 5,443,500 (Aug. 22, 1995) shows a rolled stent, comprising a rolled lattice with ratcheting mechanism. The stent mounted on an angioplasty balloon and expanded into place by force of the balloon. A pull wire threaded through the lattice of the rolled stent helps hold the stent in place on the balloon during delivery through the vasculature. Sigwart does not discuss the mechanisms and methods for delivering the stent to the target site within the blood vessel.

SUMMARY OF THE INVENTION

Stents for intra-cranial use and methods for using these stents are described in detail below. The physical characteristics of prior art balloon expandable stents and self expanding stents make them clearly unsuitable for intra-cranial use, because of their delivery profile and tendency to temporarily occlude the vessel during deployment. They have not been proposed for intra-cranial use. Palmaz stents, Palmaz-Schatz™ stents, Wallstents, Cragg stents, Strecker stents and Gianturco stents and other stents are too rigid to allow placement in the cerebral blood vessels, some require a balloon for deployment, and all are too open to occlude an aneurysm. Presented below are several embodiments of stents suitable for intra-cranial use, along with methods for using these stents to treat intra-cranial vascular disease.

The self expanding rolled sheet stent is suitable for use in the intra-cranial arteries. The rolled sheet is made of Elgiloy™, nitinol, stainless steel, plastic or other suitable material, and is imparted with resilience to urge outward expansion of the roll to bring the rolled stent into contact with the inner wall of a diseased artery. The rolled sheet is adapted for easy insertion and non-deforming radial flexibility to facilitate tracking along the tortuous insertion pathways into the brain. In some embodiments, as much of the material of the stent is removed as is consistent with eventual creation of a solid walled stent upon unrolling of the stent within the blood vessel. The unrolled stent may be two or more layers of Elgiloy™, thus providing radial strength for the stent and creating at least a slight compliance mismatch between the stent and the blood vessel, thereby creating a seal between the stent and the blood vessel wall. For placement, the stent is tightly rolled upon or captured within the distal tip of an insertion catheter. The release mechanism is extremely low profile, and permits holding the rolled stent in a tight roll during insertion and permits atraumatic release when in the proximity of the site of arterial disease, without occluding the vessel with the deployment catheter. The stent can be placed in the intra-cranial blood vessels (arteries and veins) of a patient to accomplish immediate and complete isolation of an aneurysm and side branches from the circulatory system. The stent may be placed across a target site such as an aneurysm neck, origin of a fistula, or branch blood vessels feeding a tumor in order to redirect the flow of blood away from the target. It can be used as a stand alone device which is left in the intra-cranial artery permanently, or it may be used as a temporary device which allows for immediate stabilization of a patient undergoing rupture of a blood vessel an aneurysm or awaiting open skull surgery for clipping or resection of an aneurysm. The stent can be used for stabilization and isolation of a vascular defect during surgery of the vascular defect. Another advantage of this type of stent is that it can be wound down should repositioning be required prior to full release. It is possible to rewind and reposition or remove the device using grasping tools.

The stent delivery systems described and claimed below incorporate the necessary structural modifications and features needed to provide the desired handling characteristics of an intra-cranial stent delivery system. For the most part, they are designed with the self expanding stent in mind, but they will prove useful in some applications of balloon expanding and shape memory stents. The delivery systems permit deployment of rolled sheet stents made of extremely thin Elgiloy™, nitinol, stainless steel or plastics with less concern over problems that may occur during deployment of the stent when deployed with the mechanisms disclosed in the prior art.

The delivery systems are comprised of two parts, proximal control mechanism and distal retaining and release mechanisms. For proximal control mechanisms, a slide operated by threaded knob, jack screw or trigger pull mechanism is used to provide smooth, powerful pull-back or distal pushing motion to a translating member. The translating member connects the proximal mechanism to the distal release mechanism and translates movement of the proximal mechanism into movement of the distal mechanism. The translating member can be a hypotube, stiff wire, thread, coiled or braided wire catheter or guide-wire, nylon line, micro-tubing, with rigid examples capable of providing both proximal and distal translation and flexible limp examples being only capable of distal translation. The distal retaining mechanisms provide for release of the rolled sheet stent with as little additional structure as possible, and provide for non-sliding release of the stent. The proximal removal of a sheath is not required, and the distal push of a push-rod, core, or catheter is not required, so that the rolled stent need not slide past the structures used to place the stent. This is accomplished in various embodiments by using tear-away sheaths which are operated with zip cord, a zip-strip construction common to commercial cellophane packaging, and a peeling construction. It is accomplished in another embodiment with an everting double sleeve which is pulled distally, but, by virtue of the eversion of the sleeve, does not slide over the rolled stent.

BRIEF DESCRIPTION OF THE DRAWINGS

FIG. 19 is a view of an embodiment of the stent in place within a diseased artery.

FIG. 20 is a view of an embodiment of the stent in place within a diseased artery.

FIG. 23 shows an alternative embodiment of the stent.

FIG. 24 shows an alternative embodiment of the stent in place within a diseased artery.

FIG. 25 shows a view of a tear away sheath for use in retaining and deploying a rolled sheet stent.

FIG. 40 shows a stent delivery mechanism for delivering several stents with the same delivery catheter.

FIG. 41 shows a stent delivery mechanism for delivering several stents with the same everting delivery catheter.

FIG. 42 shows a view of a tabbed stent which facilitates loading or delivery.

FIG. 43 shows a view of a tabbed stent loading or delivery mechanism.

FIG. 44 shows a view of a tabbed stent loading or delivery mechanism.

FIG. 45 shows a view of a tabbed stent loading or delivery mechanism.

FIG. 46 shows a cross section of a proximal hub assembly for use with the various catheters.

FIG. 47 shows a cross section of a proximal hub assembly for use with the various catheters.

FIG. 48 shows a cross section of a proximal hub assembly for use with the various catheters FIG. 49 shows another embodiment of a liner translator which uses a hand held electric motor.

FIG. 50 shows a cross section of a proximal hub assembly for use with the various catheters FIG. 51 shows a cross section of a proximal hub assembly for use with the various catheters.

DETAILED DESCRIPTION OF THE INVENTION

Figure 1:
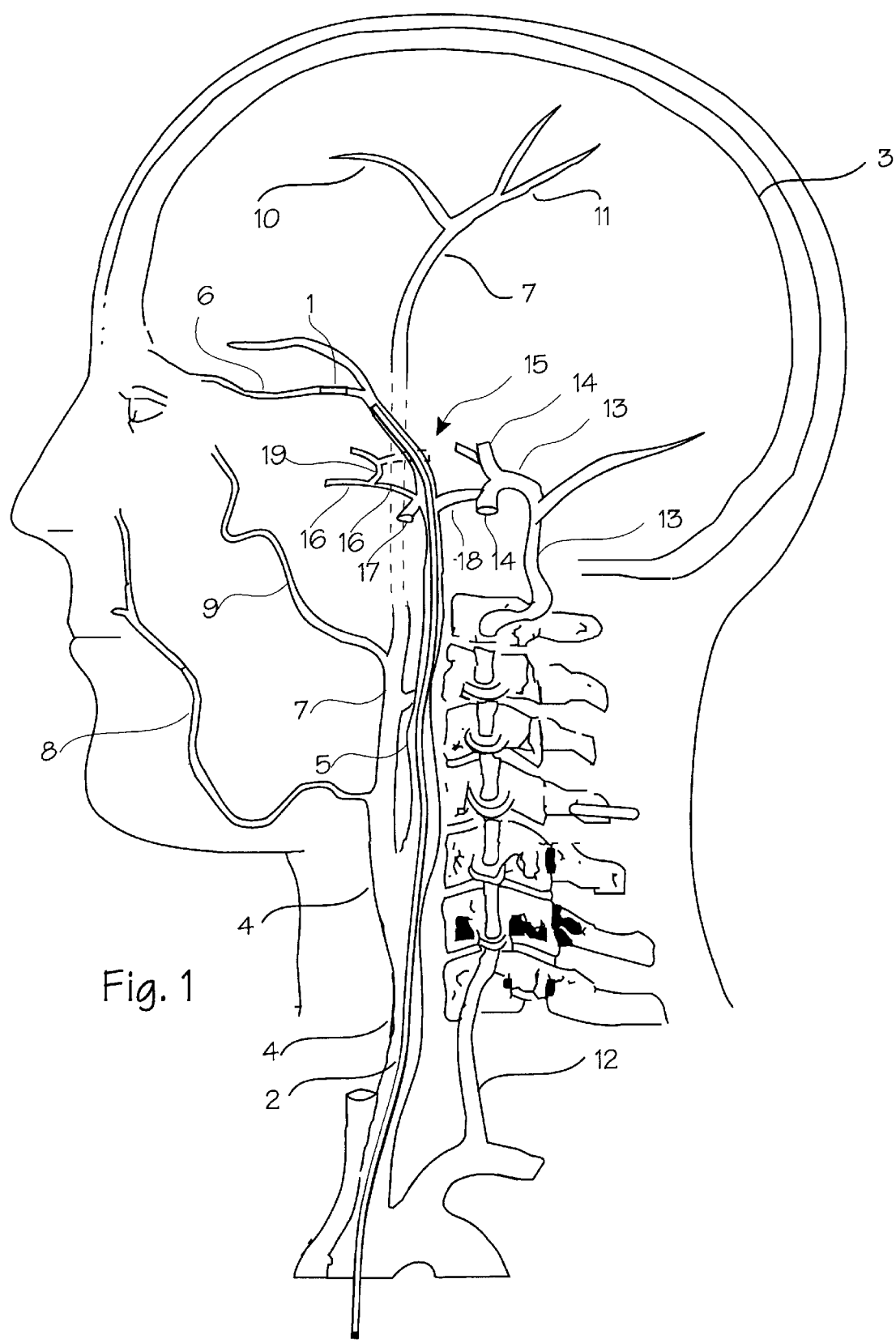
FIG. 1 is a schematic diagram of the vasculature of the brain showing a typical placement of an intra-cranial stent.
Figure 2:
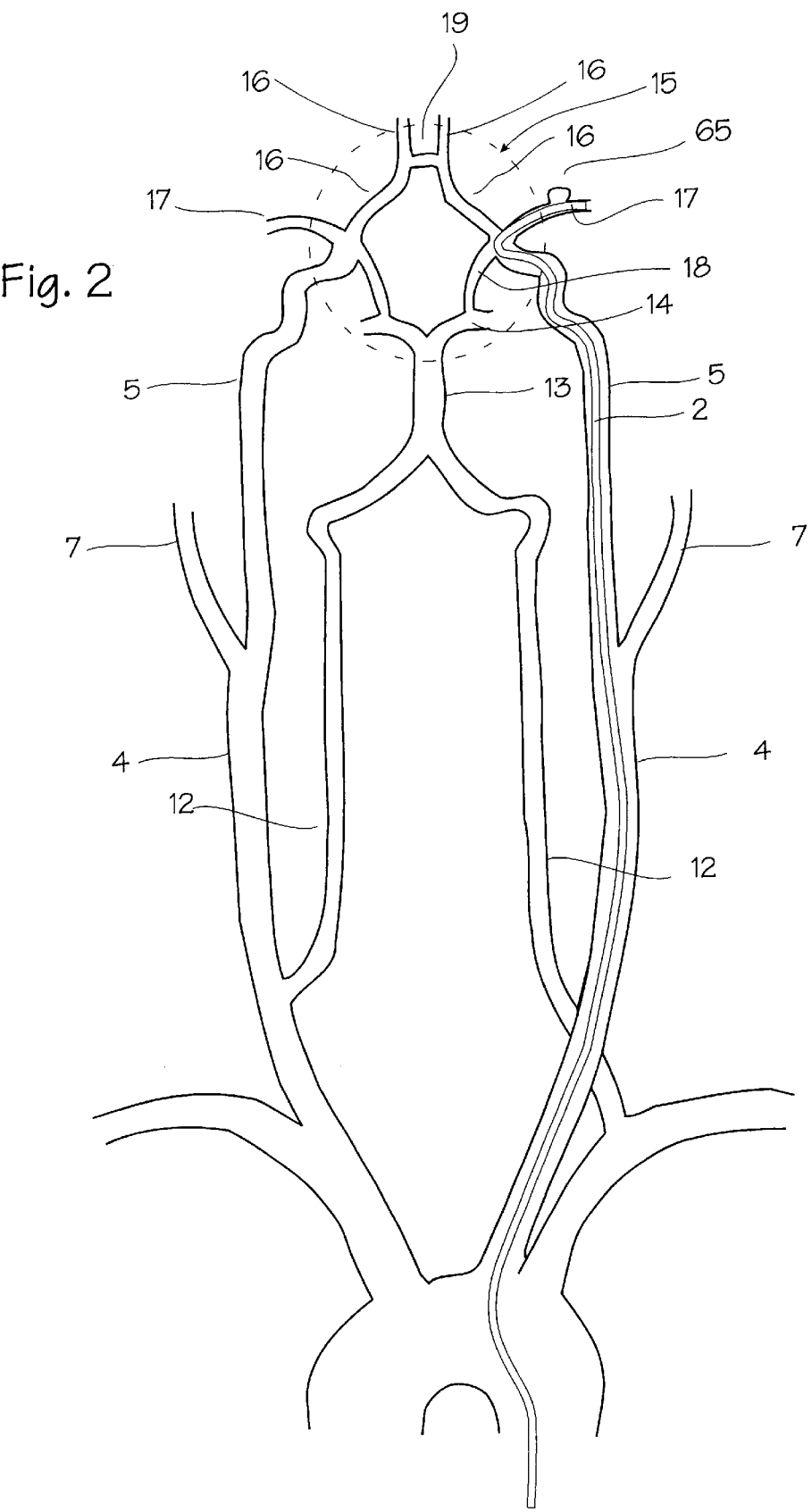
FIG. 2 is schematic diagram of the vascular of the brain illustrating the circle of Willis and arteries supplying the circle of Willis.

FIGS. 1 and 2 show the vasculature of the brain in sufficient detail to understand the invention. The brain 3 is supplied with blood through the carotid and the vertebral arteries on each side of the neck. The important arteries include the common carotid artery 4 in the neck, which will be the most common access pathway for the stent, the internal carotid 5 which supplies the opthalmic artery 6. The external carotid 7 supplies the maxillary artery 8, the middle meningeal artery 9, and the superficial temporal arteries 10 (frontal) and 11 (parietal). The vertebral artery 12 supplies the basilar artery 13 and the cerebral arteries including the posterior cerebral artery 14 and the circle of Willis indicated generally at 15. The siphon 12a of the vertebral artery appears in the intra-cranial vasculature on the vertebral approach to the Circle of Willis. Also supplied by the internal carotid artery are the anterior cerebral artery 16 and the middle cerebral artery 17, as well as the circle of Willis, including the posterior communicating artery 18 and the anterior communicating artery 19. The siphon 5a of the internal carotid artery 5 appears in the intra-cranial vasculature on the carotid approach into the Circle of Willis. These arteries typically have an internal diameter of about 1 mm to 5 mm, most commonly from 2–4 mm. The methods and devices described herein allow access to these arteries and placement of a stent in these arteries. In FIG. 1, the insertion catheter 2 and stent 1 are shown threaded through the common carotid artery 4 and the internal carotid artery 5, with the stent extending into the anterior cerebral artery 16.

FIG. 2 shows the same blood vessels in a schematic view that better illustrates the Circle of Willis and the arteries which supply this important anatomic feature. The Circle of Willis 15 is a ring of arteries connecting the internal carotid arteries and the basilar artery (and hence the left and right vertebral arteries) to the anterior cerebral arteries 16, middle cerebral arteries 17 and posterior cerebral arteries 14. The system provides a redundant supply of blood to the cerebral arteries. The carotid siphon 5a, which forms an integral part of the internal carotid artery 5, is more clearly visible in this view. Aneurysms, fistulas, AVM's and tumors occurring inside the brain, in the intracranial portion of the carotid arteries, vertebral arteries (and the portions of those arteries distal to the siphons) and basilar artery, in the circle of Willis or even deeper within the brain may be treated with the stents and delivery systems described below. FIG. 2 shows an exemplary use in which a delivery catheter 2 is inserted through the aorta into the common carotid, internal carotid, the carotid siphon and through the Circle of Willis 15 into the middle cerebral artery 17 to treat an aneurysm 65 with a stent which is held on or within the distal tip of the delivery catheter.

Figure 3:
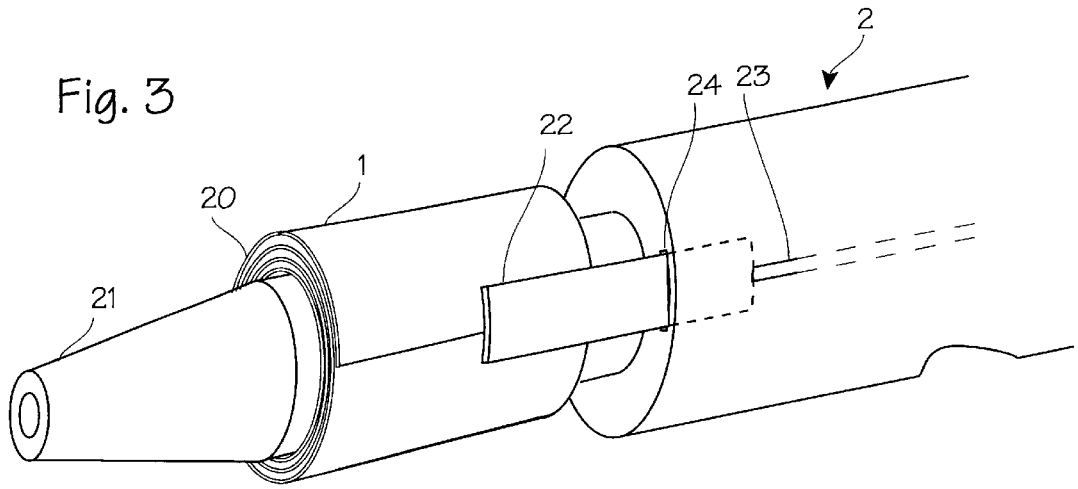
FIG. 3 is an elevational view of the rolled stent mounted on an insertion catheter.

FIG. 3 shows the overall structure of the stent 1, when mounted in the delivery catheter 2. The stent 1 is comprised of a single sheet 20 of Elgiloy™, stainless steel, nitinol, plastic or other suitable material. The metals are processed so as to provide a high level of spring property in the deployed configuration. Such processing includes cold rolling and suitable heat treatment. The stent is rolled tightly around the insertion catheter distal tip 21. Retaining clip 22 holds the sheet in a tight roll around the catheter. The retaining clip or tab is operated by pull wire 23 which extends out the proximal end of the catheter. The retaining tab is slidably disposed within the arcuate side lumen 24 and extends distally from the side lumen to hold the stent in a tight roll on the distal tip of the catheter. The retaining clip or tab 22 is operably connected to the proximal end of the catheter via a pullwire so that the retaining tab may be pulled proximally into the arcuate side lumen to release the stent. The clip mechanism provides for a lower profile than the construction of other stents such as the Winston stent and the Lane stent which require spools or sheaths. The clip mechanism may be additionally secure to the stent by folding the edge 39 of the stent over the tab so that the tab is positive engaged in a fold of stent material along the edge of the stent In another embodiment, an electrolytic charge may be used to release a securing attachment to the stent, thus allowing for stent expansion and/or release from the catheter. The clip may be made of tantalum or other radiopaque material so that it is clearly visible under fluoroscopy. The outer diameter of the stent, when rolled tightly around the distal tip of the catheter, will typically be 1–3 French (0.3 mm to 1 mm), and may be as small as 1 French, about 0.3 mm (0.012 inches or 12 mil), or even smaller. The stent may also be coated with radio-dense material (tin, tantalum, etc.) to enhance visibility under fluoroscopy. Also, radiopaque markers of tantalum, platinum or gold may be attached to the stent.

Figure 4:
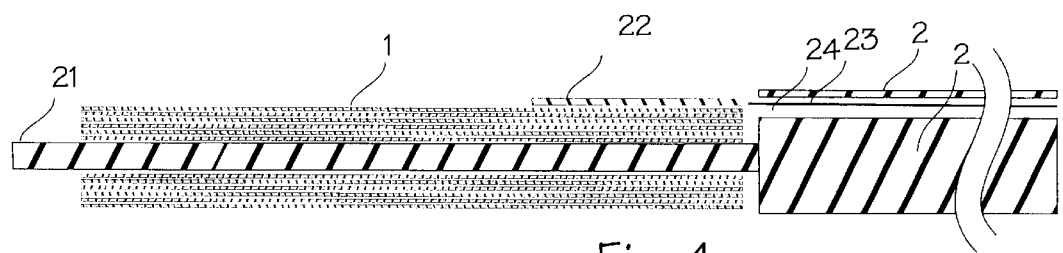
FIG. 4 is a cross section of a preferred embodiment of the stent catheter.

FIG. 4 shows the cross section of the insertion catheter 2 with the stent 1 mounted and retained by the retaining clip 22.

The retaining clip has a circumferential radius matching the outer diameter of the rolled stent, and may be pulled by pullwire 23 into the arcuate side lumen of the insertion catheter. Upon pullback of the retaining clip, the stent will release and unroll or unwind to a diameter of about 1 mm or less, or as much as 5 or 6 mm. After release, the stent will have at least one layer in the unwound state. A single layer may partially cover the interior surface of the blood vessel wall (see FIGS. 19 and 20), may completely cover the surface with a single layer of stent material, or may cover the interior surface with more than one layer of stent material. Use of multiple layers provides extra columnar and radial strength (i.e., resistance to compression or resistance to unwinding or re-rolling in response to compressive forces) vis-à-vis a single layer, and this extra strength is beneficial in view of the modifications of the stent as described below to enhance the radial and longitudinal flexibility of the stent. Another embodiment allows for a single layer stent across the vessel anomaly to be occluded and one or more layers at the stent vessel anastomosis site (the endpoints of the stent).

Figure 5:
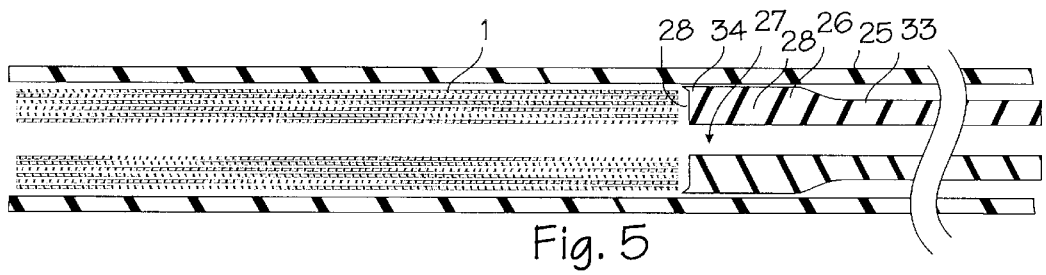
FIG. 5 is a cross section of a second preferred embodiment of the stent catheter.
Figure 6:
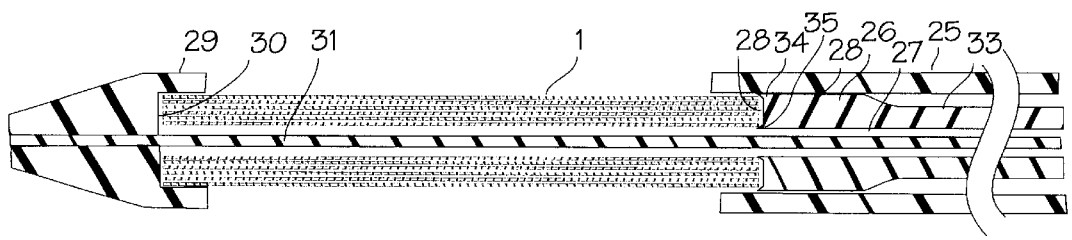
FIG. 6 is a cross section of a third preferred embodiment of the stent catheter.

FIG. 5 shows a cross section of the stent 1 mounted in an insertion catheter sheath 25. The stent is tightly rolled within the distal tip of the catheter sheath and it is delivered to the target site within the distal tip of the delivery sheath. A push rod 26 with an optional central lumen 27 and a distal face 28 abuts the proximal end of the rolled stent. In order to insert the stent within the blood vessel, the push rod 26 is used to hold the stent in place while the catheter sheath is retracted proximally to uncover the stent, or it is used to push the stent out from the sheath. Once the stent is free of the catheter sheath, it will unroll until it meets the inner wall of the blood vessel. FIG. 6 shows a cross section of a delivery catheter which provides both distal and proximal release mechanisms. The stent 1 is trapped between the push rod 26 and the distal retainer 29. The receiving bore 30 of the retainer 29 closely matches the outer diameter of the rolled stent. The internal diameter of the catheter sheath 25 also closely matches the outer diameter of the rolled stent. The external diameter of the delivery catheter is only slightly larger than the outer diameter of the tightly rolled stent. The stent is rolled tightly and trapped within the bore of the distal retainer. The distal retainer is controlled by control rod 31 which extends the length of the catheter and passes through the central lumen of the push rod 26. Preferably, the retainer control rod has an outer diameter significantly smaller than the inside diameter of the tightly rolled stent, so that it does not interfere with flexing of the stent during deployment. The retainer control rod may instead have an outer diameter equal to the inner diameter of the rolled stent, so that the stent is directly rolled around the control rod and the control rod functions as a spool or core to support the rolled stent. This delivery catheter is operated by releasing either the proximal or distal end of the stent through appropriate movement of the distal retainer, the push rod, or the catheter sheath. The stent may be released distal end first by pushing the retainer control rod in the distal direction to release the stent, or it may be released proximal end first by pushing the pushing rod forward and distally out from the catheter sheath or withdrawing the catheter sheath in the proximal direction to release the proximal end of the stent. The need for proximal-end-first or distal-end-first release will be determined during surgery, and will be accomplished as medically indicated.

The push rod 26 must fit within the catheter sheath with very close tolerances to ensure that the rolled stent is uniformly pushed from the catheter sheath and the outer roll of the stent cannot get caught between the push rod and the catheter sheath. Thus, the distal tip 32 of the push rod is enlarged relative to the proximal portion 33 of the push rod so that the distal face of the push rod has a diameter which closely matches the inner diameter of the catheter sheath. The distal face 28 of the push rod is provided with a beveled rim 34 around the outer circumference the distal face to force the stent to preferentially slip toward the center of the distal face and away from possibly interfering positions between the push rod and the catheter sheath. A beveled rim 35 may be applied also to the inside bore of the push rod (FIG. 6) to prevent the inner roll of the stent from slipping into the push rod center lumen and getting caught between the push rod and the distal retainer control rod. FIGS. 4, 5 and 6 thus illustrate means of securing the stent to the distal end of a catheter and retaining the stent in the tightly rolled configuration during insertion, and two means of inserting the stent into the blood vessel. Other means for retaining the stent include rings, pull-strings, string wraps, bars, a catheter sleeve, and electrolytic fusible joint or fusible link.

The stent may be a simple rolled sheet of Elgiloy™, nitinol, stainless steel or other resilient material. Elgiloy™ is preferred because it is less likely for the inner layer of the tightly rolled stent to take a set or become creased or crimped, which may occur in a stainless steel roll when the inner layer of the stent is tightly rolled in its deployment configuration. Plastics, bioabsorbable materials, and other materials may also be beneficially used. Polyesters, polypropylene, polyethylene, polylactic acid and polyglycolic acid are contemplated alternative materials for the stent.

Figure 7:
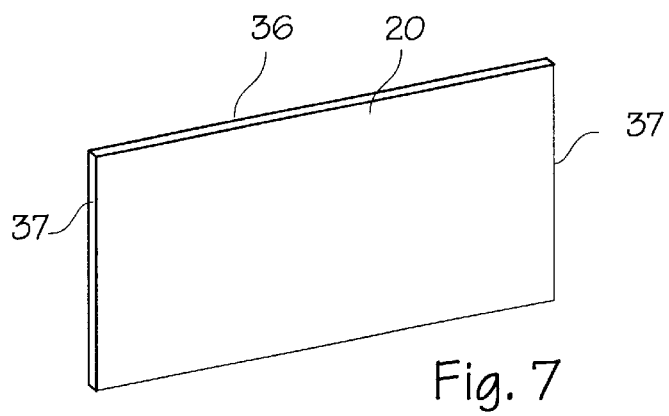
FIG. 7 is a view of a simple embodiment of the stent.

The basic embodiment comprises a sheet of Elgiloy™ about 0.0025 to 0.025 mm thick (0.1 mils to 1 mil, or 0.0001 to 0.0010 inches). Referring to FIG. 7, the wrap length represented by transverse edge 36 will be about 6–75 mm, allowing the stent to expand to diameters from about 1 mm to about 6 mm with approximately two to three layers after expansion. The bridge length represented by axial edge 37 (or the longitudinal edge) will vary according to the width of the aneurysm which must be isolated with the stent, and may vary from 2 to 20 mm, for example. The stent is tempered or formed so that it resiliently unrolls and expands to a diameter of approximately 1 mm to 6 mm, and provides a slight compliance mismatch with the intra-cranial arteries which have internal diameters of about 1 mm to 6 mm. When expanded, the stent intended for most intracranial applications will comprise a tube of one to three rolled layers. The stents described above can provide expansion ratios of five to one or greater. Expansion ratios of less than five to one may be achieved if desired. For particular intracranial applications, stents having more than three layers may be used. Stents comprising less than a single layer when unrolled will also be useful, as illustrated below in reference to FIG. 18.

Figure 8:
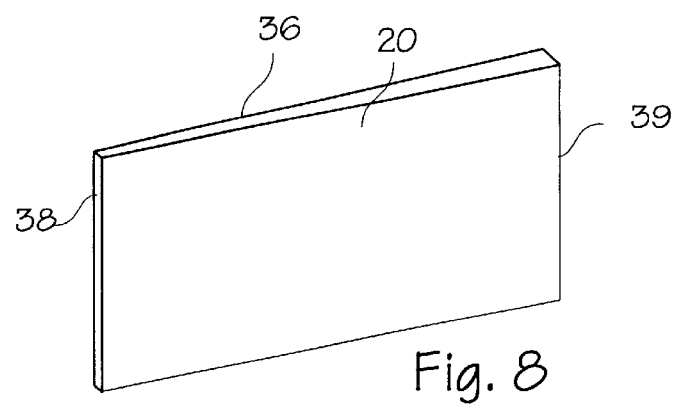
FIG. 8 is a view of a preferred embodiment of the stent.

The stent will be more flexible, and easier to bend around the various twists and turns of the blood vessels, if modified according to FIGS. 8 through 12. The stent may have a thickness which gradually increases along the transverse edge, as shown in FIG. 8. When the stent is expanded, the material of the inner layers is thinner than the outer layers.

Figure 14:
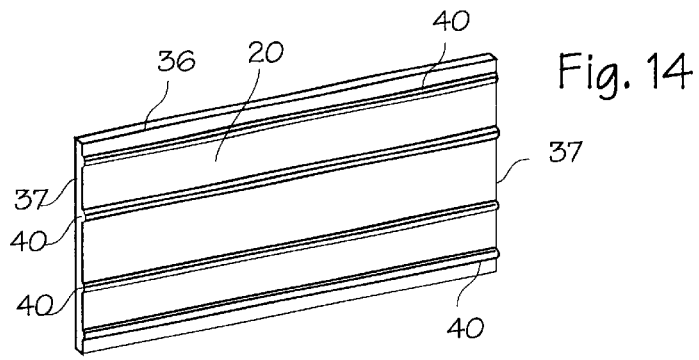
FIG. 14 is a view of an alternative embodiment of the stent.

Thus, the inner edge 38 is thinner than the outer edge 39. This construction permits the stent to flex sideways even when rolled tightly to the distal tip of the insertion catheter and mitigates the tendency of the innermost edge of the stent to be permanently deformed in its rolled down state. The inner edge may be as small as 0.0025 mm (0.1 mil), and the thickness can gradually thicken to 0.05 mm (2 mils) at the outer edge. In FIG. 14, the stent is modified with the provision of ribs 40 that extend transversely across the width of the rolled sheet, or at a slight angle to the transverse edge. The wall thickness in the interstitial portions between the ribs may be quite thin, less than 0.0025 mm (0.1 mil), and yet the stent has sufficient resilience to expand into its open configuration and exert pressure against the inner wall of a small blood vessel. This property will allow the stent to remain in position and maximize the sealing characteristics of the device. The ribs may be applied only at the distal and proximal ends of the stent, and may be integrally formed as gradually increasing stent thickness.

Figure 9:
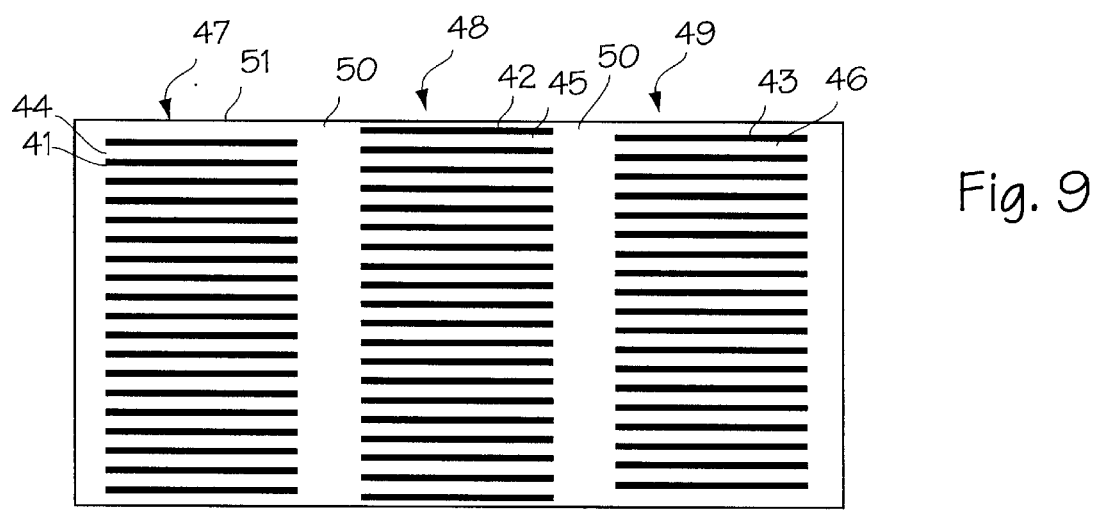
FIG. 9 is a view of a preferred embodiment of the stent.

FIG. 9 shows the stent 1 modified by excision of numerous cutaways 41, 42 and 43 leaving slats or ribs 44, 45, and 46 in eventual outer layer 47, middle layer 48 and inner layer 49. The segments of slats are separated by spines or backbones 50. The slats of each segment are offset so that, when expanded to a roll of approximately three layers, the three layers will overlap to form a barrier between the blood vessel wall and the inner lumen of the expanded stent. The slats shown in FIG. 9 are disposed laterally, aligned in the transverse direction across the width of the stent sheet, parallel to the distal transverse edge 51 or the proximal transverse edge. Of course, where the distal and proximal edges are not straight edges (such a construction may assist attachment to the blood vessel), the slats and cutaways can be described as parallel to the transverse axis of the stent sheet. The stent may be made with at least one, but preferably two layers instead of the three layers used for illustrative purposes herein, or four layers or more, and the number of layers will dictate the spacing of the slats and the cutaways. The slatted construction provides longitudinal flexibility by removing part of the material from the wall of the stent.

Figure 10:
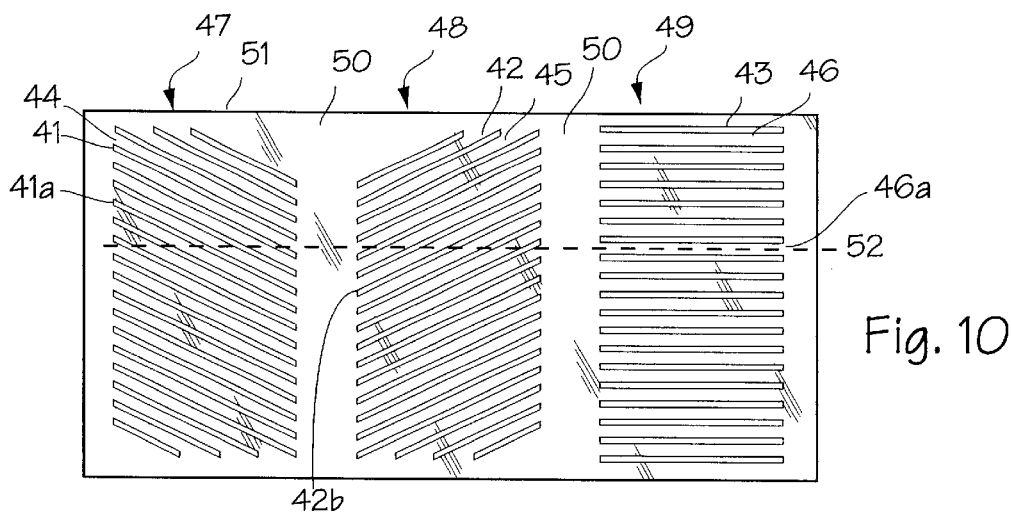
FIG. 10 is a view of a preferred embodiment of the stent.

As shown in FIG. 10, the slats may be disposed at an angle from the transverse direction and still create a barrier between the blood vessel lumen and the outer surface of the stent. In the outer layer section 47 of the stent, the slats are disposed at an angle, shown at angle of about 45° from the transverse direction. The angle of 45° is shown as one of the preferred embodiments but is to be considered merely illustrative of the infinite number of possible arrangements. In the middle layer section 48 of the stent the slats are disposed at an opposing angle, again shown merely for illustration to be about 45° from the transverse direction, but opposite the angle of the slats in the outer layer section. These two layers, when overlapping, will provide a nearly imperforate roll, with passages through the wall of the stent only at the intersections of the cutaways. These passages are, however, blocked by the transversely oriented slats of inner layer section 49. The slats are sized and dimensioned to ensure that, when expanded within the target vessel, the three layers together form a barrier between the outside of the stent and the inside of the stent. Thus if perfect three layer overlap and alignment were expected, each slat could be of equal size and the transverse inner layer slats 46 could be the same width as the passage created by the intersection of the cut-away slots in the other layers. However, to allow for an imperforate wall when the layers are not perfectly aligned and perfectly overlapping in three layers, the inner layer slats 46 are made slightly wider than the corresponding cutaways on the outer and middle layers. The dashed line 52 shown in FIG. 10 illustrates that the center point of cutaway 41a and 42b will intersect when the stent is rolled in three layers, and that slat 46a will correspond to the intersection and block the gap created by the intersection of the two diagonal slots.

Figure 11:
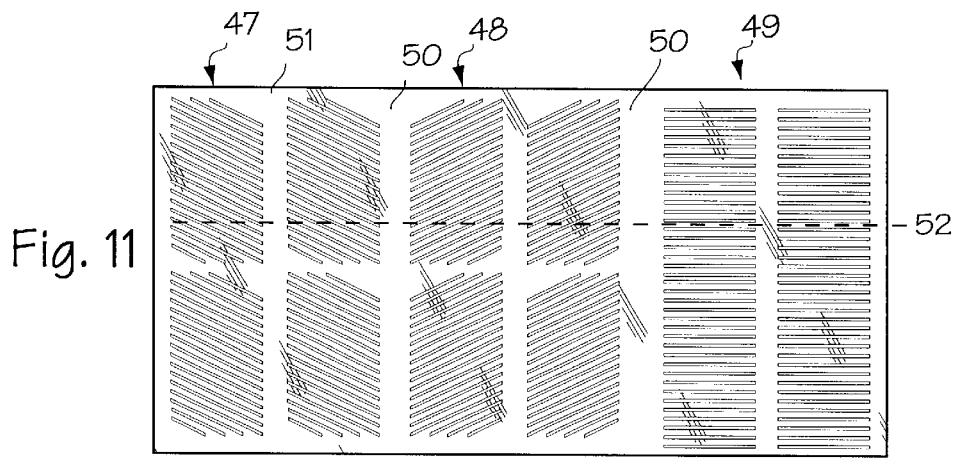
FIG. 11 is a view of a preferred embodiment of the stent.

FIG. 11 shows that numerous patterns of cutaways may be conceived to provide a multi-layered stent wherein each layer contains plurality of slots or perforations, but, when rolled so that the layers are disposed in concentric arrangement, the layers combine to form an imperforate wall. In the outer layer section, the slots are aligned on an angle from the transverse axis, while the slots in the middle layer are arranged at an opposing angle relative to the slots on the outer layer. The numerous slots on the inner layer are arranged so as to correspond to the areas of overlap of the outer and middle layer, leaving the slats to cover the open areas where the slots of the middle and outer layers overlap. Thus, FIG. 11 illustrates that the number and arrangement of slots may be highly variable while still providing an imperforate overall construction with highly perforate walls.

Figure 12:
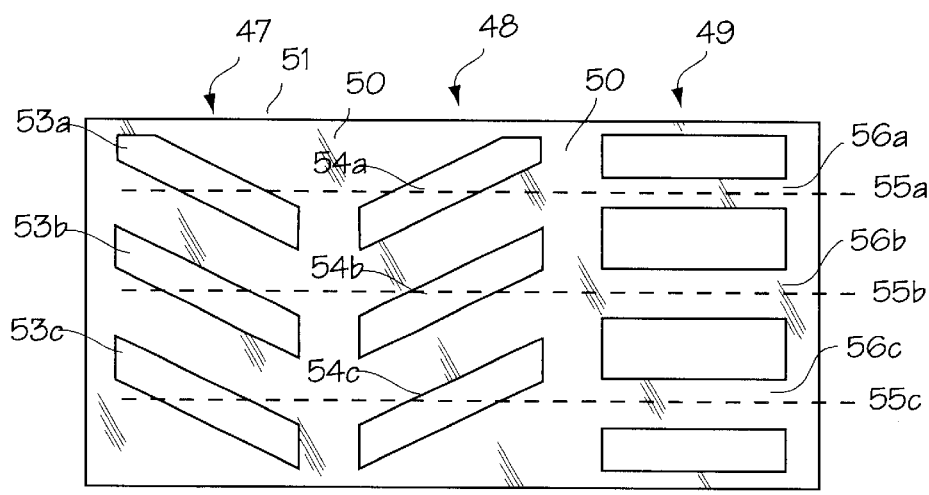
FIG. 12 is a view of an alternative embodiment of the stent.

FIG. 12 is provided as an illustration of the concept. It is more clearly demonstrated in the simple embodiment of FIG. 12 that the cutaways 53a, 53b and 53c on the outer layer and the cutaways 54a, 54b and 54c will, when the outer layer is rolled over the middle layer, intersect along lines 55a, 55b and 55c. The slats 56a, 56b and 56c on the inner layer are intersected by lines 55a, 55b and 55c, and correspond to the expected gap created by the intersection of the diagonal cutaways. The inner section slats may be made larger than the expected gap created by the diagonals to ensure blockage of the gap when the roll is either looser or tighter than exactly three layers, or misaligned. The concept may be applied to any number of layers, the general rule being that the slats of each layer, when rolled over top of each other, form an imperforate wall. Thus, the longitudinal flexibility of the tightly rolled stent is promoted by ribbed or slatted construction (or, alternatively, slotted construction) in which the various layers of the stent are provided with numerous slats which counter align when the stent is expanded to form an imperforate wall from a plurality of perforate layers.

Figure 12A:
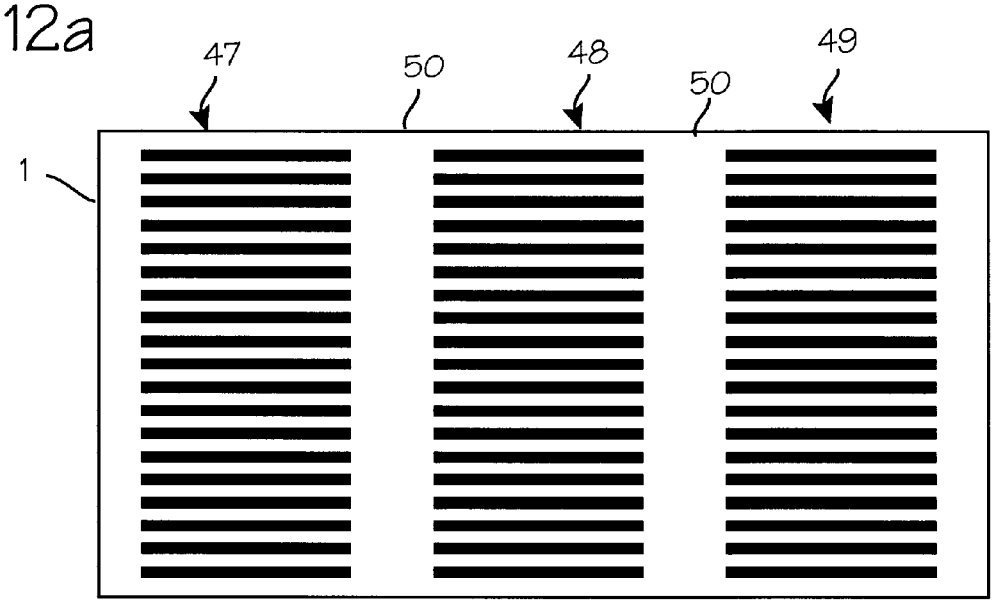
FIG. 12a is a view of a preferred embodiment of the stent.

The backbones 50 created between the slatted sections can be arranged so that they are aligned when the stent is tightly rolled, to provide increased flexibility during insertion. The backbones may also be created so that they are aligned when the stent is unrolled and deployed within the blood vessel to provide extra flexibility when unrolled in the install configuration. Careful selection of the tightly rolled size will permit alignment of the backbones during both the tight rolled insertion configuration and the loosely rolled deployed configuration. For example, if the diseased vessel for which the stent is intended is about 2 mm in inner diameter, it will have an inner circumference of about 6.3 mm (2 mm×π). A stent designed for this size vessel may have one or more segments with backbones spaced about 6.3 mm apart, so that when unrolled each segment will cover one entire circumference, and the backbones will all be on one side of the vessel. When rolled tightly to fit within the sheath or upon the distal tip of the catheter (as shown in FIGS. 4 and 5), the stent may be rolled to a diameter of 1 mm or 0.5 mm (or, for example, in relation to the preferred embodiments, any integer fraction ½, ⅓, ¼ . . . of the deployed diameter, and realizing that other relationships will apply to other embodiments), so that the backbones are layered upon each other. Thus all the backbones are disposed on one side of the roll in both the deployed diameter and the tightly wound diameter. This advantageous feature may be applied to stents having overlapping slats, and thus in the expanded configuration they will have open slots between the slats, interrupted by the overlapping backbones. Such and embodiment is illustrated in FIG. 12a, which shows the stent 1 having groups of slats 56 in the sections 47, 48, 49 interposed between backbones 50. The slats are not aligned to cause interfering blocking as shown in FIGS. 10–12, but the sections and backbones are sized and dimensioned so that the backbones line up with each other in the tightly rolled configuration to provide increased flexibility to the stent during insertion.

Figures 13, 13A:
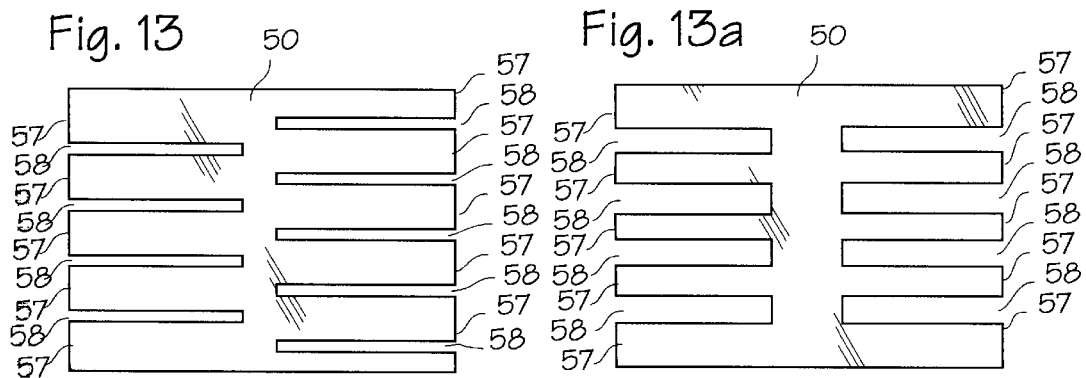
FIG. 13 is a view of an alternative embodiment of the stent.
FIG. 13a is a view of an alternative embodiment of the stent.

FIG. 13 shows another embodiment of the ribbed stent. In this embodiment, a single backbone 50 supports several ribs 57 which are unrestrained at the outer edges of the ribs. The ribs are flat and wide, with gaps 58 on one side of the backbone which are offset from the gaps on the other side of the backbone. When rolled into a tight roll (upon a catheter distal tip or inside a sheath, as illustrated in FIGS. 4 and 5), or unrolled within a blood vessel, the ribs overlap each other and form an imperforate wall. The ribs on one side of the backbone are aligned with the interstitial gaps on the other side of the backbone, thus creating an interfering pattern in much the same manner as described above in relation to FIG. 9. The backbone is the only region of this stent that is continuous from the distal end of the stent to the proximal end of the stent, and this eliminates much of the resistance to longitudinal flexibility and allows the stent to be bent around tight curves in the vasculature without crimping or creasing.

Note that by shifting any segment of slots upward or downward, the rolled stent will have a loosely rolled deployed configuration in which the walls of the stent are perforated. Thus, in reference to FIG. 9, 10, 11 or 12, the gaps closed by the slats of the third segment as described above may be maintained open by shifting slats upward or downward slightly so that they no longer block the gap. Construction of such a perforate multi-layered stent will allow flexibility of the stent in the undeployed and deployed configuration, provide for perforations allowing vessel ingrowth, better retention of the stent, or ability to pass blood into perforating vessels, yet still provide for the extra resistance to compression afforded by multiple layers.

The slots provided in the wall of the stent may be locally enlarged to create regions of highly perforate wall in the stent. This may be medically indicated when it is desired to maintain patency of the numerous side branches and perforator blood vessels which are supplied with blood by the typical intra-cranial blood vessel. In reference to FIG. 13, the circumferentially extending ribs on either side of the backbone 50 may be aligned so that the ribs on one side overlap the ribs on the other side, thereby creating openings in the wall of the deployed rolled stent which correspond to the open areas 58 between the ribs 57. This configuration in shown in FIG. 13a. The stents of FIGS. 9 through 12 may be modified accordingly, providing regions of relatively larger slots which prevent occlusive overlap of the slats, thereby maintaining patency of many side branches and perforating blood vessels fed by the stented blood vessel. This may be achieved with broad backbones and narrow slats of minimal width relative to the slots, so that occlusion is achieved only along the overlapping backbones. It may also be achieved by providing some of the slatted areas of a stent constructed according to FIG. 11 with overlapping and occluding dimensions while providing other slatted areas with dimensions which result in a highly perforate, non-overlapping or completely patent structure in the loosely rolled deployed configuration.

Figure 15:
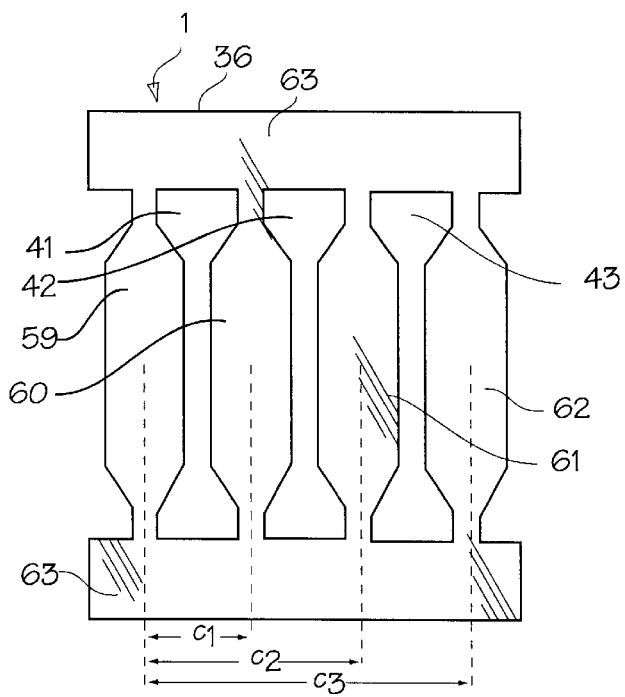
FIG. 15 is a view of an alternative embodiment of the stent with slats running in the longitudinal direction.

Another embodiment of the rolled stent is shown in FIG. 15. This stent is a variation of the slatted stent illustrated above. The slats are aligned longitudinally in relation to the catheter and blood vessel, and perpendicular to the transverse edge or wrap length 36. The slots 41, 42, and 43 are narrow relative to the slats 59, 60, 61 and 62. To create a loosely rolled stent in a substantially imperforate wall from this stent, the wrap length 36 is several times longer than the circumference of the target blood vessel. When the stent is loosely rolled to approximate the inner diameter of the blood vessel lumen, the gaps between longitudinally oriented slats in one layer will be blocked by the slats in other layers. Occlusion of the stent wall will occur for all vessel circumferences which are approximately equal to the distance between the center of one slat and the center of one slot. Thus an imperforate wall is formed from this highly perforate embodiment of the rolled sheet stent for vessels with diameters corresponding to lengths $C_1$, $C_2$, and $C_3$, equivalent to the distance from the reference slat 59 to the center of each of the various slots. The bar-bell shape of the slots (cutaway portions) creates fusiform or tapered shaped slats joined to the end bands 63 provides additional flexibility for the stent when tightly rolled to fit within (or upon) the distal tip of the delivery catheter.

Figure 21:
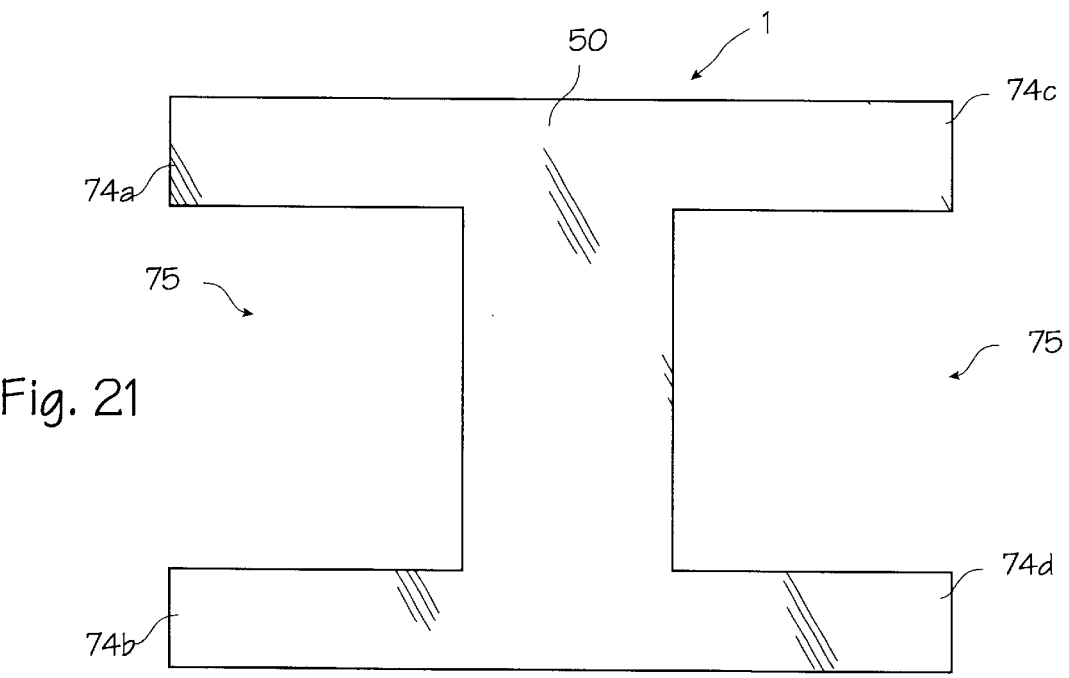
FIG. 21 shows and alternative embodiment of the stent.

In relation to each of the embodiments described above, the stent may be configured to provide a section (either an arcuate segment or a longitudinal segment, which is substantially imperforate, while the remaining portions of the stent are substantially perforate or open. This allows for occlusion of the aneurysm or target site of disease while permitting flow of blood between the vessel wall and the blood vessel lumen in other areas of the stent. This allows blood flow to any branch blood vessels or perforator blood vessels which supply blood to the brain. The "H" shaped stent of FIG. 21 accomplishes this, and variations on the alignment of the slot patterns on the multi-layered stents of FIGS. 8 through 12 will accomplish such an arrangement.

All of the stent configurations are intended for use while visualized under fluoroscopy. Fluoroscopy will also be used to view the stent during follow-up to ensure continued proper placement. Thus the stent may be coated with radiopaque material such as tantalum to enhance visibility under fluoroscopy. The stent may be coated with a number of substances which help prevent thrombus or coagulation of blood around the stent or in the nearby blood vessel which may be affected by the stent. Paralyne, polyurethane, polyester, polyphosphazene, Dacron, Nylon, silicone, polymers and biopolymers, heparin and albumin coatings, negative ion coatings, tin, and acids such as polylactic acid and polyglycolic acid may be used. Various medications may be bound to the coating, and medications such as heparin, methotrexate, forskolin are contemplated for use. The surface of the stent may also be made microporous with perforations of, for example, about 0.001" diameter to enhance the vessel ingrowth into the stent for better stent/vessel attachment and to improve thrombogenicity.

Figure 16:
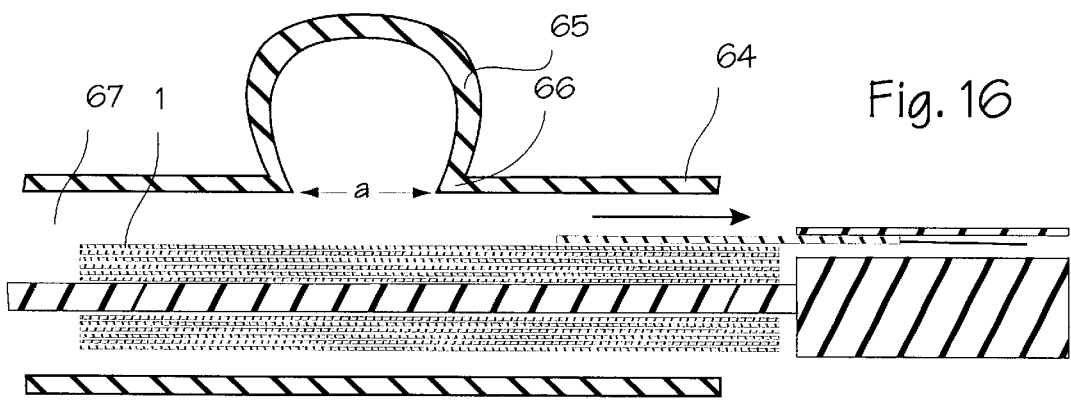
FIG. 16 is a cross section of diseased artery with the stent in place.

The stent is placed with the insertion catheter into an artery within the skull or brain, such as the many arteries pointed out in reference to FIG. 1. The catheter is inserted into a blood vessel of a patient, typically the femoral artery, and the distal tip with the stent mounted thereon is steered into an intra-cranial blood vessel of the patient. In the close-up view of FIG. 16, the stent is shown in an artery exhibiting an aneurysm which could rupture or lead eventually to occlusion, both life threatening events. The blood vessel 64 includes a saccular aneurysm 65. The aneurysm and aneurysm neck may vary in size. Small aneurysms are those of 0–10 mm diameter. Large aneurysms are 10–25 mm in diameter, and giant aneurysms are greater than 25 mm in diameter. Distance a represents the size of the aneurysm neck.

In clinical discussion, a wide-neck aneurysm has a neck which exceeds 4 or 5 mm. The stents described herein may be used with aneurysms of all sizes.

Figure 17:
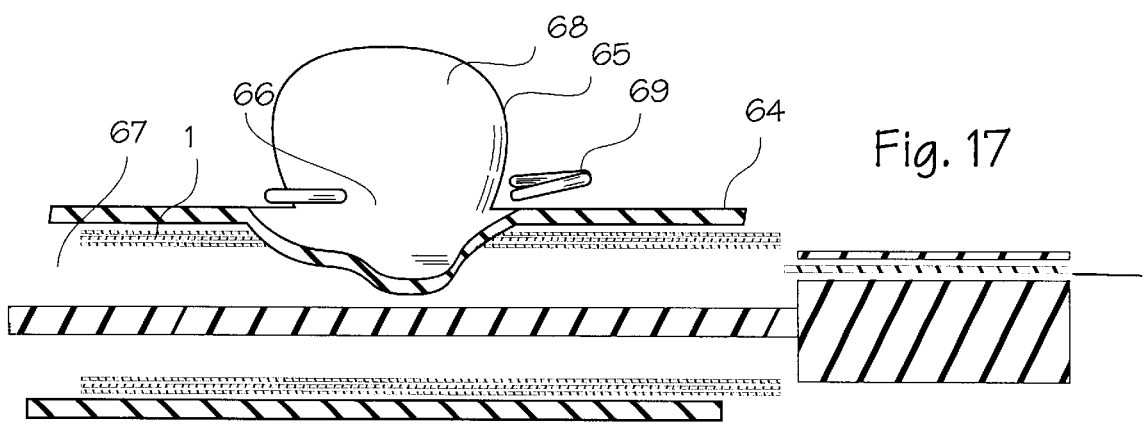
FIG. 17 is a sectional view of a diseased artery with the stent being used in conjunction with aneurysm clips.

The placement of the stent 1 straddles the aneurysm. Once in the diseased portion of the intra-cranial artery, the stent is maneuvered into place in the proximity of the aneurysm, with the stent straddling or bridging the neck 66 of the aneurysm. Once in position, the retaining clip is pulled back into the side lumen thereby releasing the stent within the intra-cranial artery. The solid walled stent, or the modified stent, unrolls to form an imperforate barrier between the arterial wall and the center of the stent, and immediately isolates the sac 65 from the blood vessel lumen 67. This is shown in FIG. 17, in which the stent has unrolled from an original tightly rolled configuration shown in FIG. 16 to a partially unrolled configuration with three layers of stent material.

Upon placement of the stent, the blood flow is redirected from the target opening and the aneurysm is isolated from the high blood pressure of the vascular system, and the threat of hemorrhage is eliminated. In this manner, a patient showing signs of acute distress from a cerebral aneurysm may be treated immediately in a manner that stops or prevents rupture and hemorrhage. Placement of the stent immediately seals off the aneurysm to protect against bleeding or rupture, in contrast to prior art open walled stent placements used in larger peripheral arteries which require significant time for the formation of fibrous tissue within the aneurysm and formation of endothelial cells to create a barrier which isolates the aneurysm from the high pressure of the vascular system. Gradual retraction of the aneurysm or tumor after exclusion and resultant lack of blood flow should relieve any mass effect caused by the size and pressure of the aneurysm or tumor against other structures in the brain.

Figure 18:
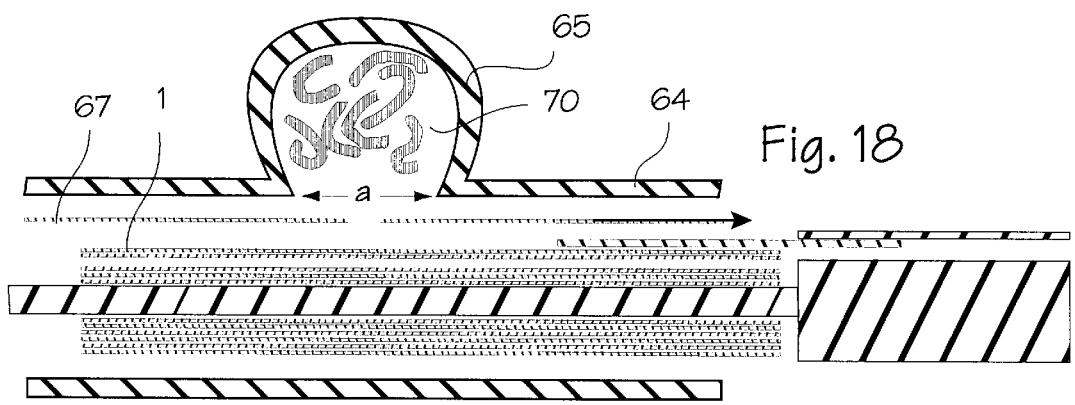
FIG. 18 is a sectional view of a diseased artery with the stent being used in conjunction with detachable coils.

The stent may be left in place as the permanent treatment for the aneurysm or target vessel, or it may be used as a temporary means of re-directing blood flow for stabilizing a patient while considering or actually performing more invasive treatment. Aneurysm clipping, which is one of the standard treatments for intra-cranial aneurysm, is plagued by the risk of rupturing the aneurysmal sac during the surgery. As shown in FIG. 17, the aneurysm may be clipped in accordance with known procedures while the stent is in place. To place the clips, the brain must be exposed and dissected away from the aneurysm so that the clips may be placed at the base of the aneurysm. Rupture during surgery makes the surgery more difficult, decreases visibility and requires additional dissection, contaminates the brain with blood, and makes it more difficult to seal the aneurysm with the clips. With the stent 1 expanded within the blood vessel, the brain is dissected away from the aneurysm to expose the outside 68 of the aneurysm. Clips 69 (shown in FIG. 17) may be placed at the neck of the aneurysm and squeezed closed upon the aneurysm, thereby further sealing the aneurysm sac from the blood vessel. After the aneurysm has been successfully clipped and thereby isolated from the high pressure of the blood vessel, the stent may optionally be removed from the lumen of the blood vessel. FIG. 18 shows that the stent may also be used to immediately isolate the aneurysm after placement of GDC's. Several Guglielmi detachable coils or other such detachable coils 70 are shown inside the aneurysm sac 65. The coils will, in the usual case, eventually cause coagulation and clotting within the aneurysm. However, the patient is at risk during the period required for successful development of the occluding mass caused by the bodies reaction of the coils. To ensure immediate isolation of the aneurysm from the blood vessel, and to ensure that the coils do not escape the aneurysm sac and float downstream to cause embolization or clotting in healthy portions of the blood vessel, the rolled stent is deployed immediately before or after placement of the coils. When used in this manner, the stent is used as an adjunctive to surgery to make it safer and eliminate the complications arising from invasive surgery. In cases where a patient is presented in an emergency condition, perhaps suffering from a ruptured intracranial aneurysm, immediate placement of a solid walled or slightly perforate stent may be the only way to save the patient's life while preparing for other surgery. Placement of coils may be accomplished through the wall of the stent, where the stent is slightly perforate (with a high metal to vessel wall ratio) or where the coils may be pushed into the aneurysm through slots in the wall of an imperforate stent constructed according to FIGS. 9–16.

FIG. 19 illustrates another embodiment of the stent as well as another method of using the stent to isolate an aneurysm 65 from the blood stream. The stent 1 has been inserted into the blood vessel 64 and covers the opening of aneurysmal sac 65. A blood vessel 71 (it may be a branch that is supplied by blood vessel 64 or it may supply blood vessel 50) joins blood vessel 64 near the aneurysm. A rolled stent which unrolls to cover all 360° of the blood vessel inner wall will cover both the aneurysm and the blood vessel 71, but it is usually desirable to maintain flow to or from this blood vessel. In this case, a stent 1 with a short wrap length is used. The stent has a wrap length which is shorter than the internal circumference of the blood vessel, so that when unrolled within the blood vessel it expands to meet the inner wall of the blood vessel but covers less that the entire circumference of the blood vessel wall. The elasticity and spring force of the stent will hold it in position against the blood vessel wall and isolate the aneurysm from the blood vessel. FIG. 20 illustrates another situation where the resilient half stent is used. The blood vessel and branch blood vessel are normal and healthy. Another branch vessel 72 supplies blood from the main blood vessel 64 to a diseased area 73. The diseased area may be an aneurysm or fistula in the branch blood vessel, a tumor supplied by the branch blood vessel, or any other vascular disease. The half stent has been released within the main blood vessel 64 so that it blocks blood flow to the branch blood vessel, thereby isolating the diseased area from the blood stream. The diseased area will necrose and be absorbed by the body over time, thereby alleviating the condition without surgery directly in the area of the disease.

When used in this manner in a perfectly round blood vessel, the stent must have a wrap length of at least half the inner circumference of the blood vessel so that it covers at least 180° of the inner wall of the blood vessel. However, in a real blood vessel which is not perfectly round, it may be sufficient that the wrap length be about half the inner circumference of the blood vessel, and cover about 180° of the inner wall, and coverage of at least 180° will be useful in a wide range of blood vessels. In use, it will be most practical to select a wrap length which results in about 210° to 270° of coverage (with wrap length corresponding to about ¾ of the expected inner wall circumference), to ensure a good fit, adequate resilience for expansion and holding power, and sufficient clearance for the branch blood vessel.

The half layer stent shown in FIGS. 19 and 20 may be provided as a single imperforate sheet, or it may include any pattern of slots as illustrated in FIGS. 6–9. The half layer stent should be mounted on the catheter distal tip (FIG. 4) or within the catheter sheath (FIG. 5) so that it is properly aligned with the side branch or aneurysm to be blocked. The retaining clip made of tantalum (or other radiopaque material) or a tantalum marker on the sheath will provide the reference point for the surgeon during placement, so that rotational and longitudinal alignment with these markers will allow proper release and placement of the stent. The rolled stent may be centered under the retaining clip so that the clip corresponding to the side of the vessel where the stent is to be placed.

Figure 22:
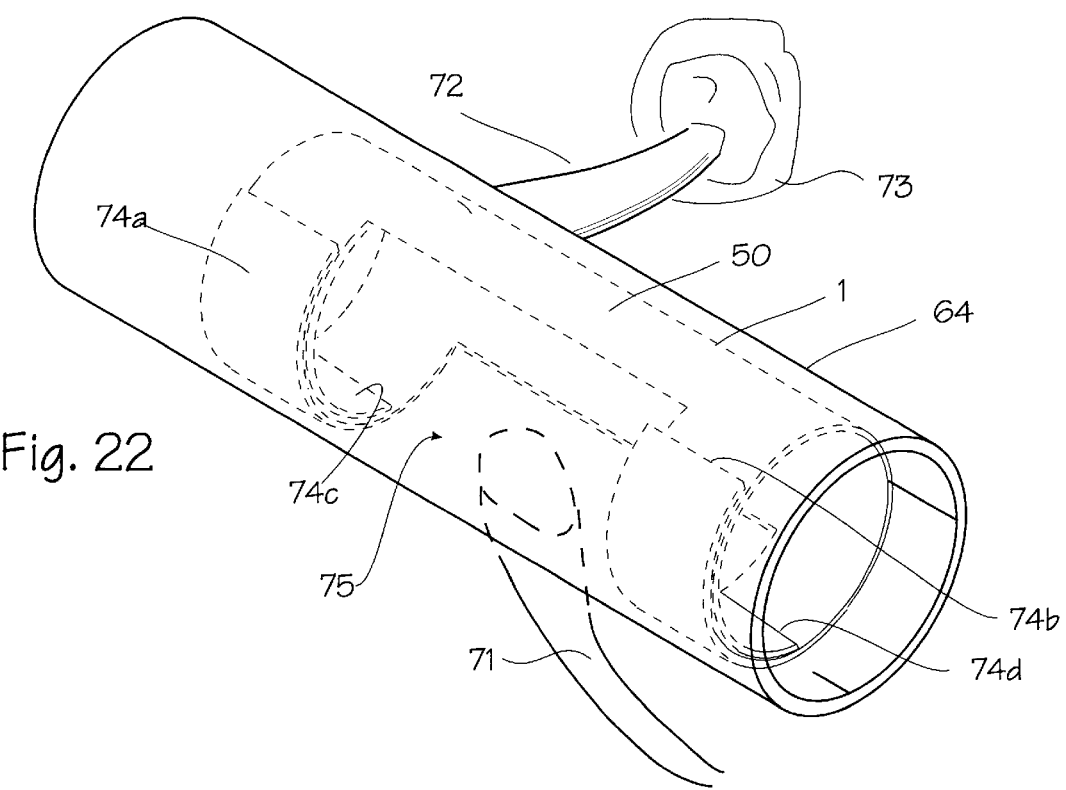
FIG. 22 is a view of an embodiment of the stent in place within a diseased artery.

FIG. 22 shows another variation of the stent. This stent is shaped like the letter "I" or the letter "H." The backbone 50 is augmented with integrally formed ribs or tabs 74 extending transversely from the backbone at the distal and proximal ends of the stents. The transversely extending tabs create open areas 75 The transverse edge preferably exceeds the circumference of the blood vessel in which the stent is inserted. The single backbone will provide the occluding surface area of the stent, while the ribs serve to provide radial expansive strength for the stent to provide stronger deployment and holding resilience.

As shown in FIG. 22, the loosely rolled deployed configuration of the stent has the backbone 50 occluding the target vessel 72, while the ribs or tabs extend circumferentially over the entire circumference of the blood vessel to hold the stent in place. The ribs may overlap somewhat, as shown, creating an arcuate open space 75 in what would otherwise be the wall of the stent. Branch blood vessel 71 is not occluded because the stent is placed so that the cutaway portions of the stent overlie the opening into the blood vessel 64. Thus, in use, the stent provided with an occluding sheet with transversely extending retaining bands on the distal and proximal ends is placed within the blood vessel so that the occluding sheet occludes a diseased branch vessel, aneurysm or other AVM while circumferential portions of the blood vessel opposing the occluding diseased branch vessel, aneurysm or other AVM are not covered by the occluding sheet, thereby allowing blood flow between the blood vessel and any branch blood vessel communicating with the blood vessel at a site opposite the occluding sheet.

FIGS. 23 and 24 illustrate another embodiment of the rolled sheet stent. This stent takes the shape of an open frame with an open central area 76. Side-frame pieces 77a and 77b will provide the occluding surface for this stent, and distal end and proximal end pieces 78 will provide radial support for the stent. When rolled within a blood vessel as shown in FIG. 24, the overlapping side frame pieces occlude the diseased branch vessel, aneurysm or other AVM designated generally at item 73. As with the stent of FIG. 21, this stent is placed within the blood vessel so that the open portion overlies the healthy branch vessel 71 while the occluding sheet made up in this instance of side frame pieces covers the diseased blood vessel 72. In FIG. 24, several perforator vessels 79 are shown to illustrate that there will typically be several perforators left open and unoccluded by the open area of the stent, while other perforators, such as perforator 80, may be occluded by the stent. In the deployed configuration, the stents of FIGS. 22 and 24 will appear to be very similar, comprising an arcuate occluded segments and an arcuate unoccluded segments. The occluded segment is created by the spine 50 in FIG. 22 or side pieces 77a and 77b in FIG. 24, and the unoccluded segment is created by the central opening 75 or 76.

The stents described above are very flexible, and exhibit a highly independent longitudinal structure (that is, the ends of the stent are very independent, and constraint of one end will not cause restraint of the other). The delivery systems described below are useful for deploying these stents within the body while minimizing the need to force the components to slide past the stent material. One embodiment of a non-sliding stent deployment mechanism is illustrated in FIG. 25. FIG. 25 shows a rolled sheet stent 1 mounted on the tip of an insertion catheter 2 and restrained by a thin tear-away sheath 81. Starter notches 82 are cut in the tear-away sheath to ensure that tearing is easily initiated. Cords 83 are looped over the entire length of the tear away sheath, and are initially set in the starter notches. The loops 84 extend from the proximal end of the tear-away sheath to the distal end of the sheath, and the cord is then routed into the central lumen 85 of the insertion catheter 2 through side ports 86. The cord may be secured to a pullwire 87 residing within the insertion catheter and operable from the proximal end of the catheter. The insertion catheter may be a microcatheter having a lumen or it may be a guide catheter or guide-wire such as a hollow cross wound guide catheter.

Figure 26:
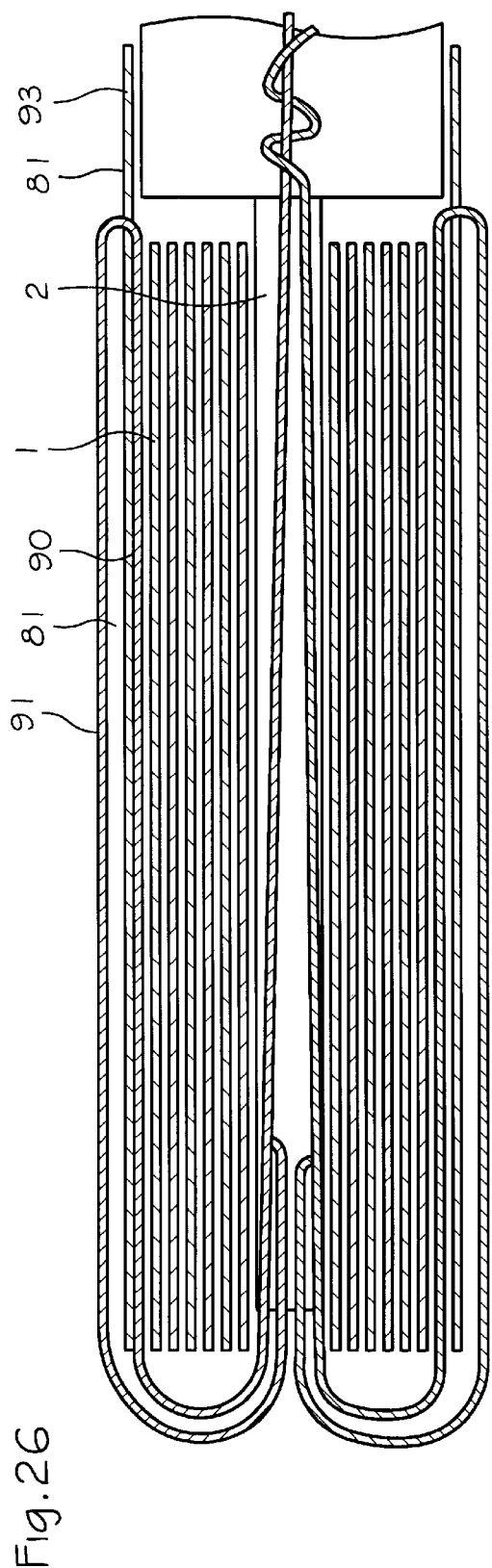
FIGS. 26 and 27 show a cross section of the tear away sheath assembly.
Figure 27:
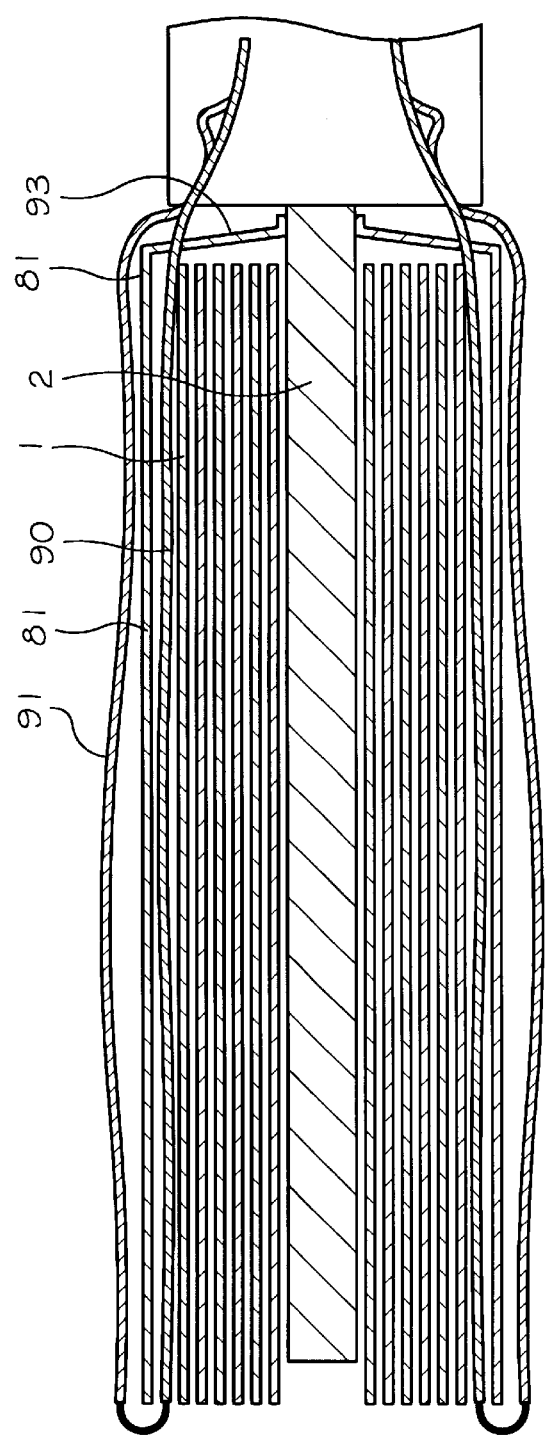

FIG. 26 shows this construction in cross section, where the multiple layers of the rolled stent are shown constrained by the tear-away sheath 81, and the cords 83 are visible within the cross section of the catheter. The underlying cord segment 90 (the segment that runs under the sheath) may be tied to the overlying cord segment 91, in which case the entire loop will move over the stent and operate to tear the sheath 81. Instead, the underlying cord segment can be secured to distal end of the sheath or the inner lumen of the insertion catheter, and not to the overlying cord segment. In this case, only the overlying segment will move distally upon pullback of the pullwire while the underlying segment will not move relative to the stent, except as it is lifted and pulled away from the stent as the loop rolls forward in response to the pullback. FIG. 27 shows an alternative construction of the tear-away device where the zip cords are routed into a guide sheath 92 which may be used with the delivery catheter. Note that in both FIGS. 26 and 27, the sheath is provided with a proximal extension 93 which can serve to secure the stent to the insertion catheter 2. The loops and pull cord perforate through the sheath where necessary for attachment to the pullwire.

In FIG. 27, the tearing progresses from the distal end of the tear-away sheath to the proximal end of the tear away sheath, in contrast with the construction of FIG. 26, in which pulling the zip cord in the proximal direction results in distal movement of the loops because the cord is directed out the distal end of the catheter before being engaged in the tear-away sheath. In these embodiments, the tear away sheath is made of 0.0001 to 0.001 in. plastic tube such as heat shrinkable PET. The loops and cords may be made from any suitable cord, line, wire or suture material. The stent 1 may be any of the stents describe herein, or other prior art stents. The insertion catheter 2 may be a small diameter catheter tube or a guide-wire which is steerable within the vasculature. Where the insertion catheter is comprised of a guide wire, the guide wire with the stent mounted on the distal tip may be steered to the target site without the aid of an addition guide-wire.

Figure 28:
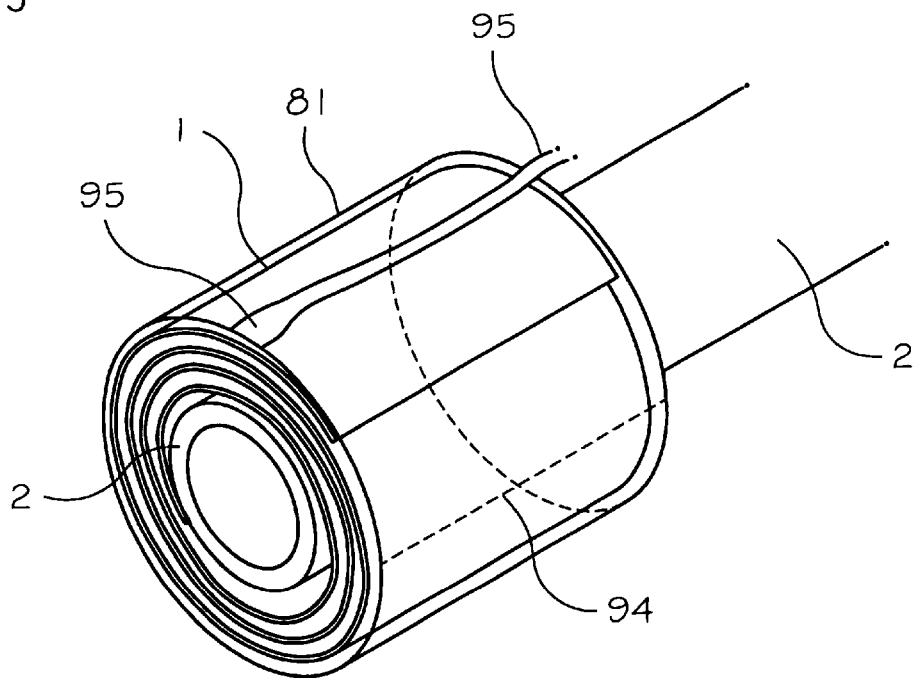
FIG. 28 shows a view of a peeling sheath mechanism for use in retaining and deploying a rolled sheet stent.
Figure 29:
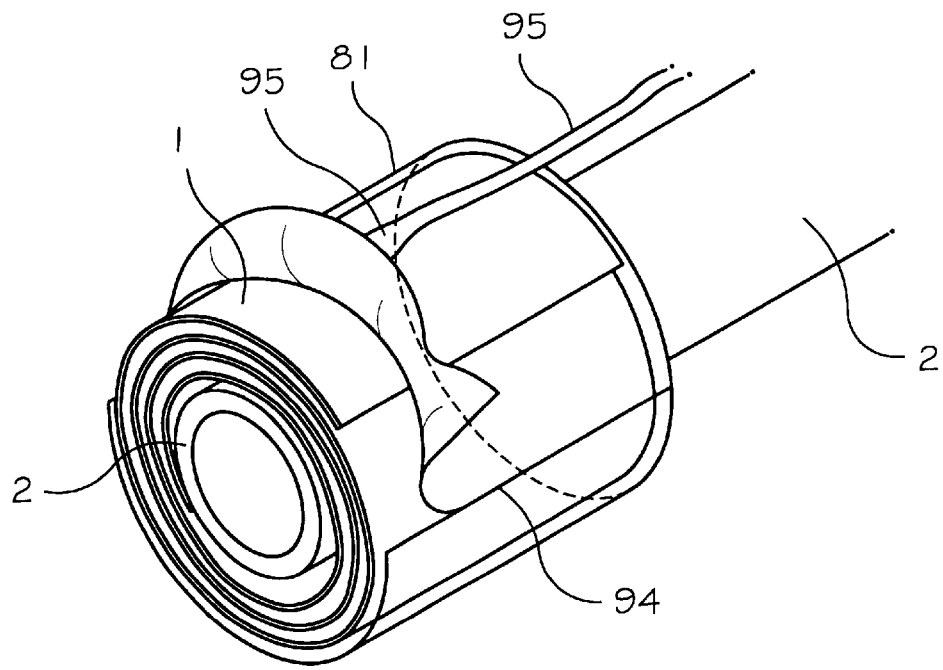
FIG. 29 shows a second view of a peeling sheath mechanism for use in retaining and deploying a rolled sheet stent.
Figure 30:
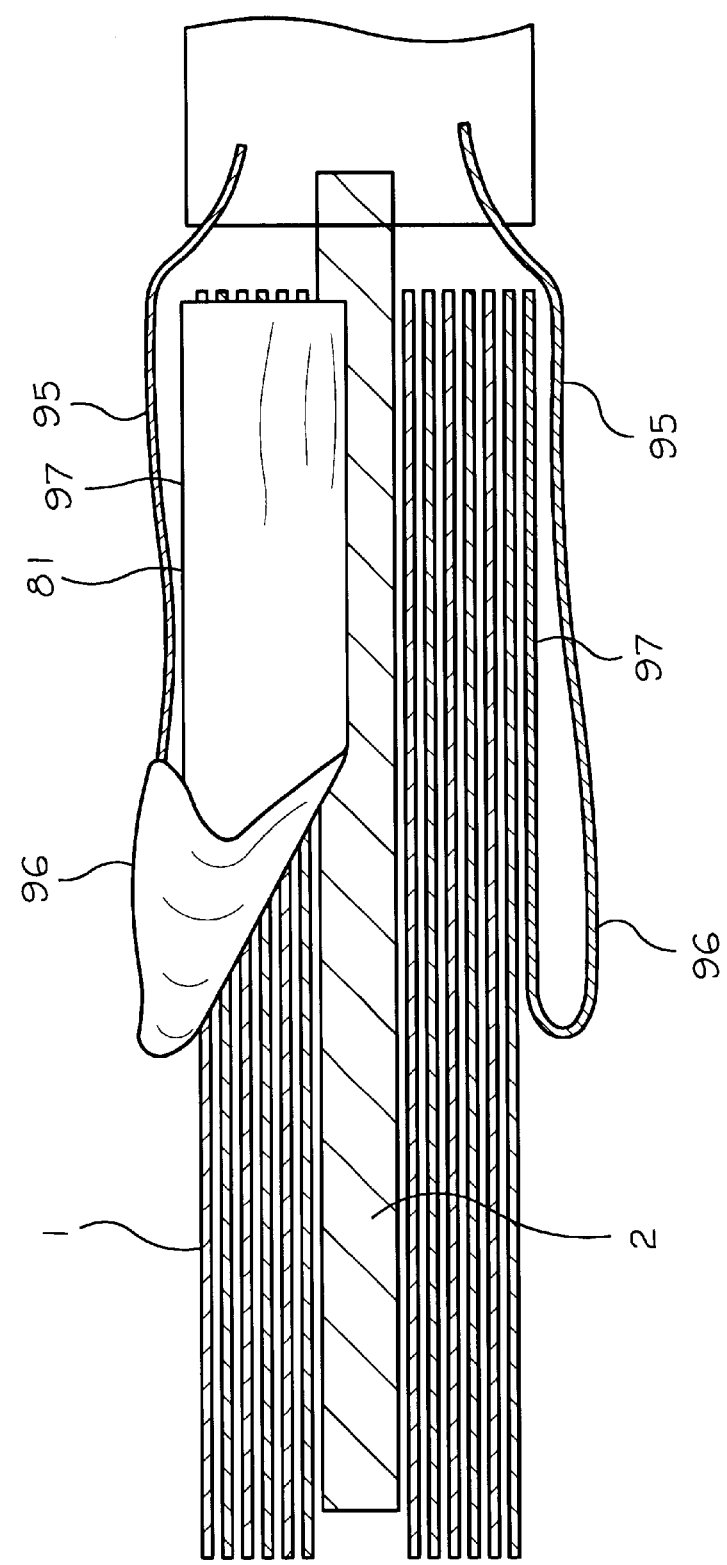
FIG. 30 is a cross section of a peeling sheath mechanism for use in retaining and deploying a rolled sheet stent.

FIG. 28 shows a non-sliding deployment mechanism for the rolled sheet stent. This mechanism operates like a banana peel. The tear-away sheath 81 in this embodiment surrounds the stent 1 and holds it in a tight roll at the distal tip of the catheter 2. The catheter may or may not include a distal core or spool for support of the stent. Where a distal core is used, it may be comprised of the distal portion of a guide-wire which allows the entire assembly to be steered into the target site. The sheath is scored with one or more perforation lines 94, and preferably has two such perforations lines located 180° apart on the sheath. A pull tab 95 is integrally formed with the sheath 81, and connects to the sheath at or near the distal edge of the sheath and extends to the proximal end of the catheter, or it may connect to a pullwire near the distal tip of the catheter 2, so long as it is operably connected to a pulling control mechanism on the proximal end of the catheter. The sheath 81 is removed from the stent by pulling the pull-tabs in the proximal direction. As shown in FIG. 29, when the pull-tabs 95 are pulled proximally, the sheath tears along the perforation lines 94 and the sheath 81 is peeled away from the stent like a banana peel. The cross section shown in FIG. 30 illustrates that the sheath 81 folds backward over itself, and peeling section 96 moves relative to the stent, while the unpeeled proximal 97 section of the sheath need not move relative to the stent and the stent need not move relative to the catheter 2. As more clearly shown in FIG. 30, two pull tabs are provided and arranged circumferentially about the sheath, and any number of pull tabs may be provided. The amount of sliding between the sheath and the stent is minimized in this embodiment. When completely unpeeled, the sheath 81 may be withdrawn with the catheter 2.

Figure 31:
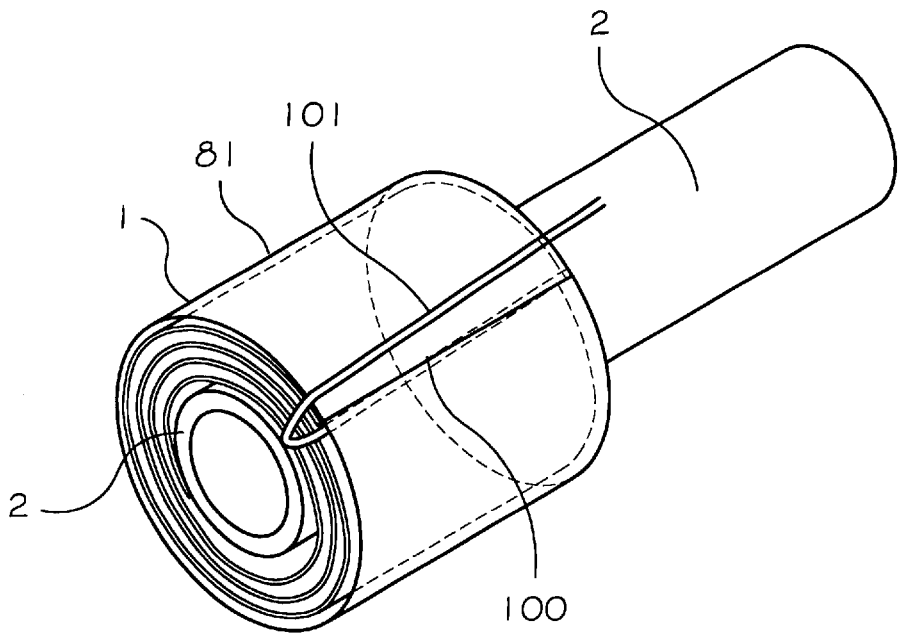
FIG. 31 shows a view of a zip-strip mechanism for use in retaining and deploying a rolled sheet stent.
Figure 32:
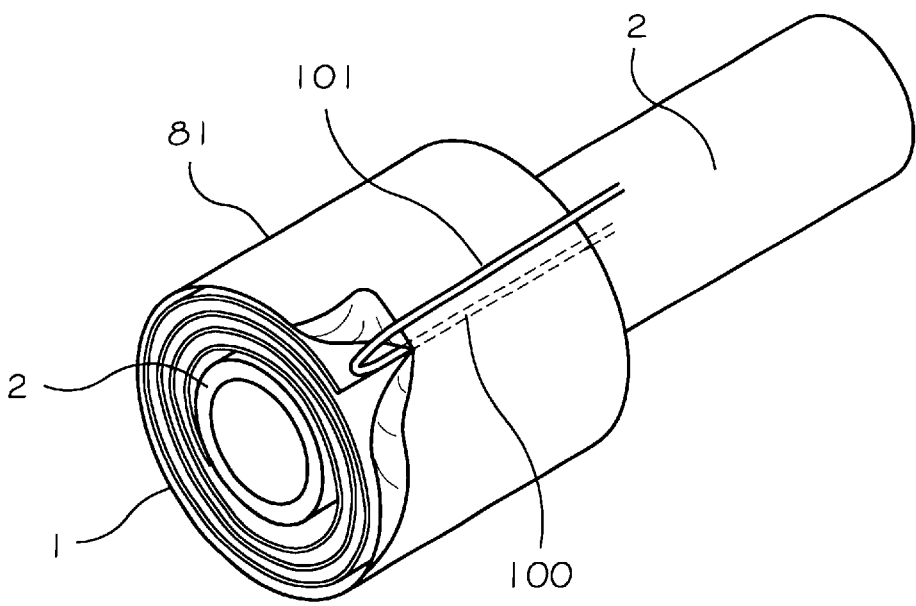
FIG. 32 shows a second view of a zip-strip mechanism for use in retaining and deploying a rolled sheet stent.

FIG. 31 shows a non-sliding deployment mechanism for the rolled stent. As in the previous figures, the sheath 81 surrounds the stent 1 and holds it in a tight roll at the distal tip of the catheter 2. The catheter may or may not include a distal core or spool for support of the stent. The sheath 81 is provided with a zip-strip 100 which is connected to the pull-strip 101 which may be integrally formed with the zip strip 100. The pull-strips are connected to a proximal pulling mechanism. The zip-strip, pull strip and sheath are constructed in a manner similar to zip-strips used commonly for cellophane wrapping on cigarette packages, CD cases, express mail envelops, etc. FIG. 32 illustrates the zip-strip mechanism of FIG. 31 after the zip-strip has been partially pulled back. The sheath 81 is torn along the zip strip as the pull-strip is pulled away from the stent. The stent is gradually uncovered as the tear progresses along the sheath, and there is no need to cause the stent to slide past the sheath. The sheath may be pulled into the delivery catheter or it maybe left in place between the stent and the blood vessel.

Figure 33:
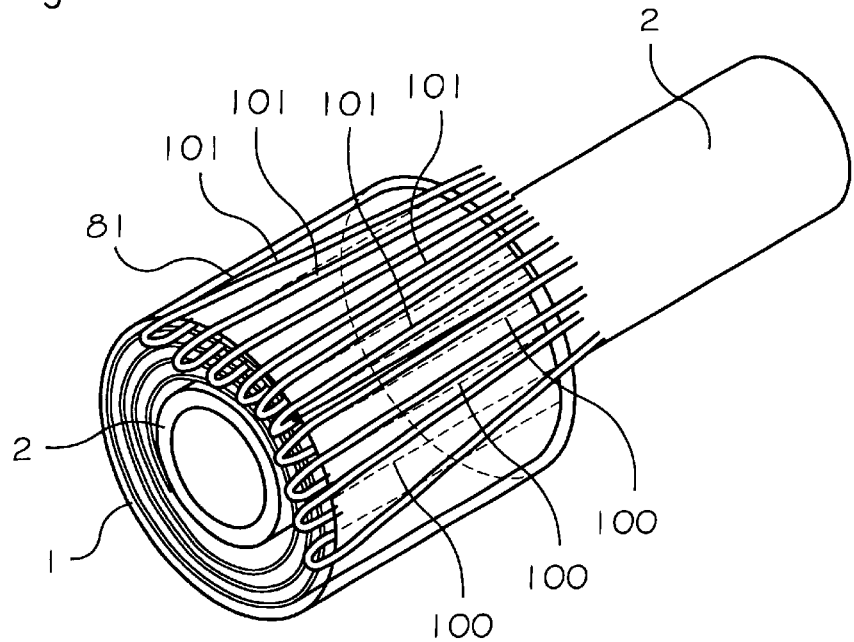
FIG. 33 shows an alternative embodiment of the zip-strip mechanism using a number of zip-strips.

The zip-strip mechanism can be modified as shown in FIG. 33, where a number of zip-strips 100 are placed under the sheath 81 so that substantially the entire circumference of the sheath overlies a zip-strip. Each zip-strip 100, shown in phantom because they lie underneath the sheath 81, is a separate strip secured by adhesive, heat seal or otherwise, to the overlying sheath 81. When all the pull-strips 101 are pulled proximally, the sheath is torn into shreds corresponding to the underlying sip-strips. The embodiment facilitates removal of the entire circumference of the sheath after release of the stent. Depending on the surrounding vasculature, the stent may release before all strips are pulled completely off the stent. When these strips are caught between the stent and the blood vessel wall, they may be removed by continued pulling on the strips. Due the number of strips, any sheath remaining between the stent and the blood vessel wall may be removed in a peeling or everting action, rather than sliding over the outer layer of the stent. The plurality of zip-strips may also be comprised of a single sheath which is scored or perforated to form a plurality of zip-strips weakly connected or unconnected along the perforations.

Figure 34:
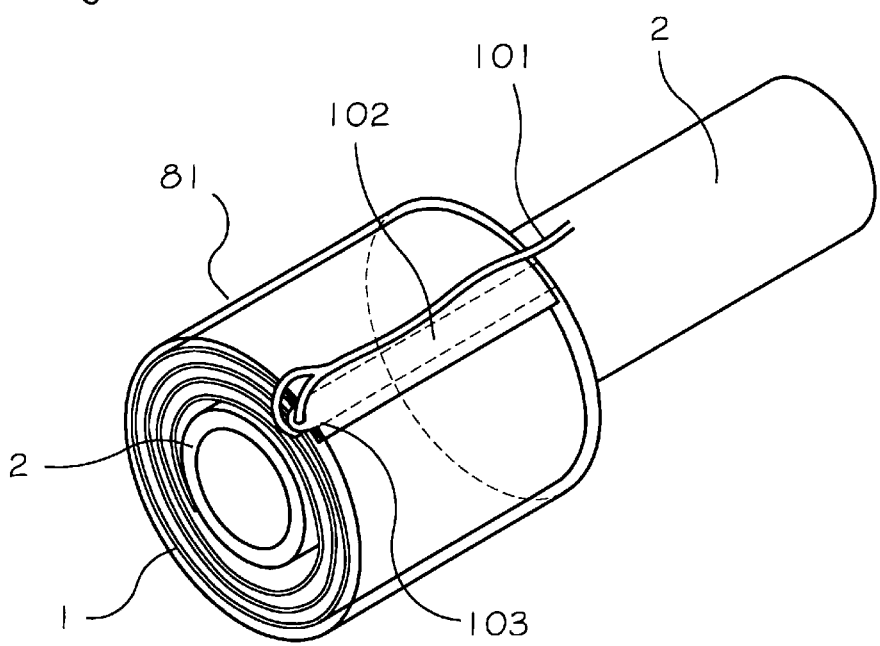
FIG. 34 shows an alternative embodiment of the zip-strip mechanism for use in retaining and deploying a rolled stent.

FIG. 34 shows an alternative construction for the zip-strip. Whereas in FIG. 31 a cord is placed under the sheath, and tension on the cord results in tearing of the sheath, in FIG. 34 the cord is made integrally with the sheath, and is constructed by scoring lines on the sheath to form the strip 102. Starting notches may be used in place of full length scoring lines. The pull cord 101 is tied to the strip at extending tab 103. As with the other embodiments, proximal tension on the pull strip acts to tear the strip 102 away from the sheath, thereby releasing the stent.

Figure 35:
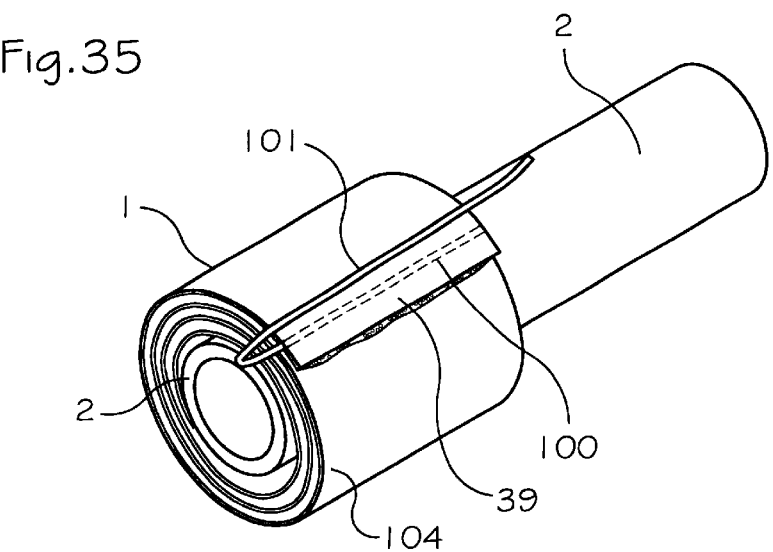
FIG. 35 shows an alternative embodiment of the zip-strip mechanism for use in retaining and deploying a rolled stent.
Figure 36:
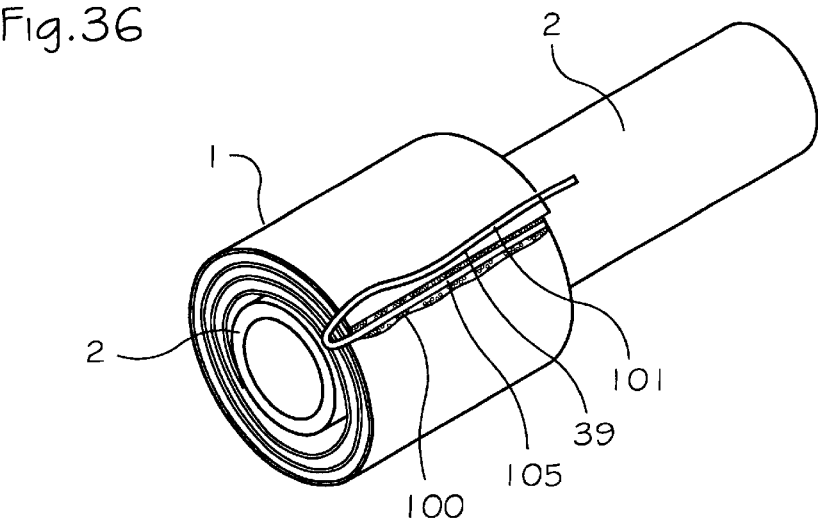
FIG. 36 shows an adherent bead mechanism for use in retaining and deploying a rolled stent.
Figure 37:
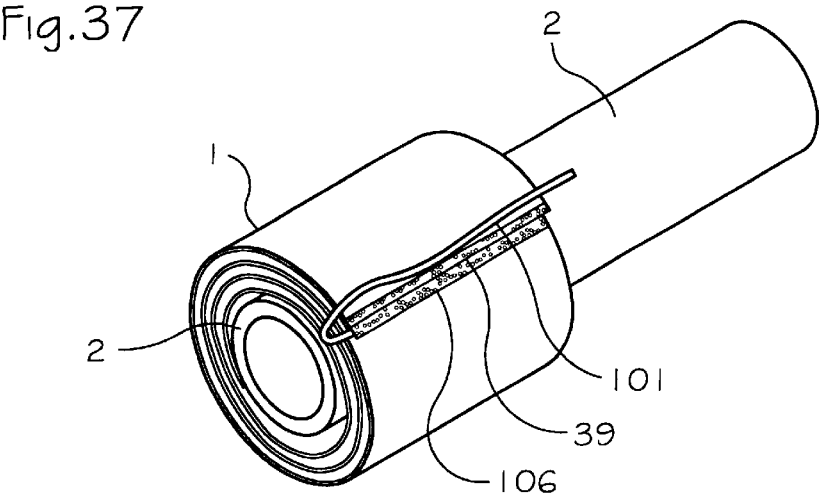
FIG. 37 shows an adhesive strip mechanism for use in retaining and deploying a rolled stent.

FIGS. 35, 36, and 37 show embodiments of the rolled stent in which the sheath is replaced with an edge binding in which the outer edge of the stent is glued, taped, soldered, or welded to the underlying stent layer. FIG. 35 shows an example of such an embodiment. The outer edge of the rolled stent 1 is sealed to the outer surface of the outer layer 104 which lies underneath the edge 39. The stent thus forms a sealed roll of stent material.

The zip-strip 100 is placed under the outer wrap of the stent and attached to the pull strip 101. The stent material is pre-scored as shown by the dotted lines to facilitate tearing. When the zip-strip is pulled proximally, the outer wrap is torn neatly along the scored line, and the stent unrolls. In this embodiment, there is no sheath remaining, and only the pull-strip and zip-strip are left for removal through the catheter. The tape may be formed of pre-formed polyester tape, or may be formed by painting a strip of silicone, co-polymers, UV curable polyurethanes, for example, which may be applied in liquid or flowable form and removed in a cohesive strip.

FIG. 36 shows a similar self expanding stent secured to the distal tip of catheter 2. A joining bead 105 joins the outer edge 39 of the stent 1 to the underlying layer, similar to the bead shown in FIG. 34. The zip-strip 100 is placed under the bead, so that the zip-strip will tear the bead when pulled, thereby releasing the stent. A bead of polyester will adhere sufficiently to the stent to provide retention, and will yield readily to the tearing force of the zip-strip. FIG. 37 shows yet another variation of the edge binding release, wherein an adhesive strip 106 is used to tape the edge of the stent down to the underlying layer. The tape is secured to pull cord 101, which is operated from the proximal end of the catheter to pull the tape away from the stent.

Figure 38:
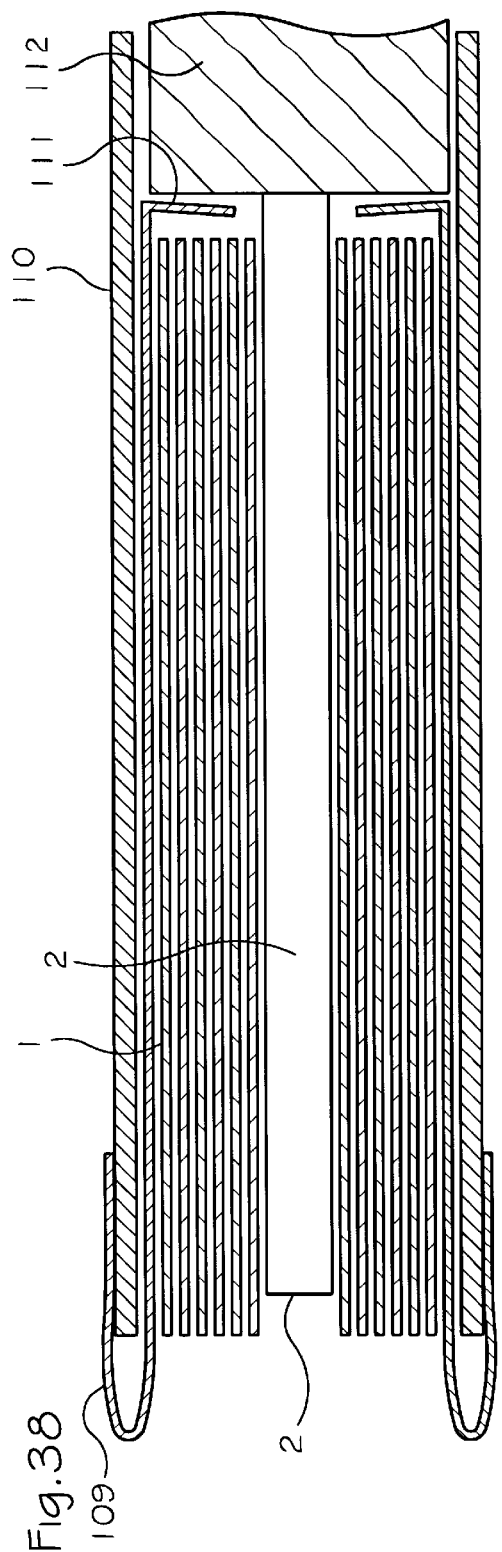
FIG. 38 is a cross section of the everting delivery mechanism.
Figure 39:
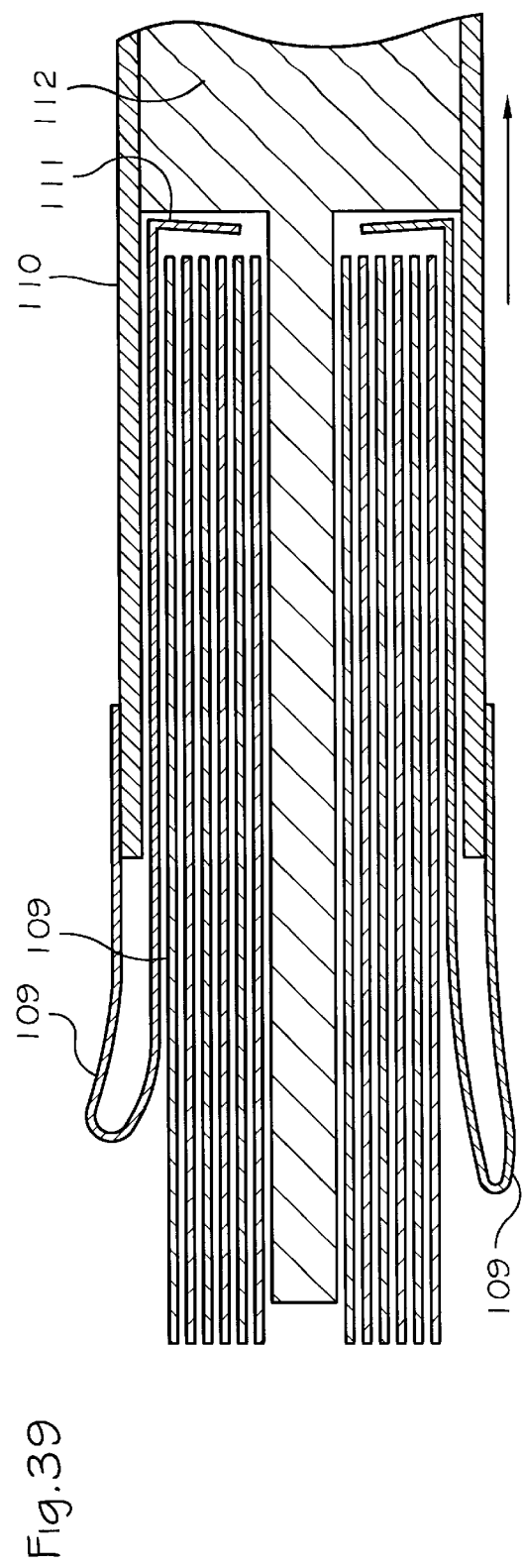
FIG. 39 is a cross section of the everting delivery mechanism with the retaining sleeve partially everted.

FIG. 38 shows yet another non-sliding everting deployment mechanism for the rolled sheet stent. The stent is rolled tightly within an everting sheath comprised of a very thin plastic sleeve 109, and may be rolled about the catheter 2, which in this embodiment may be a guide-wire used to place the stent at the target site. The sleeve 109 is not secured to the stent except by virtue of the tight fit. The sleeve is secured to the distal end of the sheath 110, and may have in inward wrap 111 at its proximal end to isolate the catheter core 112 from the stent and prevent the thin walls of the stent from slipping into any clearance between the catheter core and the sheath. The catheter core 112 keeps the stent from moving proximally within the sheath. The stent is released when the sheath 110 is pulled back from the stent (as indicated by the arrow in FIG. 39) thereby pulling the sleeve over and off of the stent. The sleeve 109 is everted (turned inside out) as the catheter sheath is pulled back. When pull-back is complete, the stent will be released and the sleeve will be inside out.

Each of the release mechanisms described above may be used to deploy multiple stents from the same delivery catheter. This may be desirable in cases where several aneurysms or AVM's are encountered in close proximity to each other. FIG. 40 shows a delivery system similar to that shown in FIGS. 25 through 27. Several stents 1a, 1b, and 1c are shown mounted on delivery catheter 2, which also includes a support core 113. The stents are retained in the tightly rolled condition by the tear-away sheaths 81a, 81b and 81c. The cord 83 is shown looped over the sheath, and run under the sheaths 81a, 81b and 81c. A second cord may be placed on the opposite side of the catheter. The cord is routed into the lumen of the delivery catheter through port 114, and extend to the proximal end of the catheter where it is connected to pulling mechanisms. As illustrated, a pair of cords may be used to tear each segment of sheath from each stent. One pair of cords may operate to tear a single long sheath which covers all three stents away from each stent, or a separate pair of cords and a separate length of sheath may be provided for each stent. The operation of this stent delivery mechanism is similar to the operation of the single stent delivery mechanism, with the cords being pulled proximally in this case, to tear the sheaths along pre-weakened tear lines. The sheaths may be secured to the core with bands 115 to facilitate their removal after expansion of stents. In similar fashion, the everting sheath delivery catheter of FIG. 38 may be loaded with more than one stent. This embodiment is shown in FIG. 41, where several stents 1a, 1b, and 1c are shown mounted on everting delivery catheter 2. As the everting sheath 109 is withdrawn, the stents are released one at a time. The zip-strip delivery catheter of FIG. 31, and the peel-away delivery catheter of FIG. 28, may also be constructed to hold and deliver a plurality of stents disposed within the sheath at the distal tip of the catheter.

Loading the stents onto the distal tip of the catheter is facilitated by the construction and method illustrated in FIGS. 42 and 43. The rolled sheet stent 20 which makes up the stent 1 is provided with a pair of ears or tabs 116, one on the distal edge of the stent and one on the proximal end of the stent. Each tab is provided with thread hole 117 through which a retaining cord may be threaded. The pull cord 101 is threaded through the thread holes and secured to the delivery catheter 2, as shown in FIG. 43. As shown in FIG. 44, the cord is used to hold the stent in place while the sheath 81 is applied. The stent is covered with an appropriate sheath, which may be any sheath disclosed herein or in the prior art. The sheath may be applied by heat shrinking a material such as PET over the stent. Other retaining structures may be applied, such as the adhesive bead or strip shown in FIGS. 36 or 37 (tape). The ears or tabs may be snipped off the body of the stent after the sheath has been put in place over the stent, as illustrated in FIG. 45. The cord may remain in place to be used as the tear away cord. While the holes are placed in the tabs to best facilitate rolling of the stent on the catheter, the holes shown in the tabs may be moved into the main body of the stent, and penetrate through all layers of the stent. It should be recognized that the intermediate embodiments shown in FIGS. 43 and 44 may be used as a final embodiment, wherein the retaining cord is used as a pull cord. The tabs may be left in place or snipped away in such an embodiment. The pull cord may be secured with any releasable mechanism, such as a detente, a breakable joint or electrolytic joint. A single pull cord may be used, threaded through both thread holes, or a separate pull cord may be used for each tab. Just as tabs 116 facilitate tie down of the outer edge of the stent, tabs may be added to the inside edge 38 to facilitate initial placement of he stent inside edge upon the insertion catheter 2.

Each of the stent release mechanisms illustrated above require a proximal hub assembly which includes controls for pulling or pushing the various pull cords or push rods. The hubs may be referred to generally as linear translators, as they translate various turning, twisting, squeezing, and other motions into linear motion of the pull cords or push rods. The hub assembly is preferably hand held and easily operated to impart appropriate pulling or pushing forces on a longitudinal member such as the pull cords, push rods, or the catheter sheath. Thumb slide assemblies commonly used in pull-wire steerable catheters may be used, but the frictional forces between the sheath and the pull cords can be variable and surprisingly high. The proximal hub assemblies disclosed below are designed to provide smooth longitudinal pulling or pushing force, and, where possible, to allow one-handed operation. FIG. 46 shows a proximal assembly designed to provide the longitudinal movement needed in the various stent retaining devices. The hub 118 includes a barrel 119 with a central bore 120 which houses the various portions of the catheter. The delivery catheter proximal end 121 includes the guide catheter or guide sheath 92, the delivery catheter 2 disposed within the guide catheter, and the zip cords or pull-wire 87 are disposed within the delivery catheter. A sliding traveler 122 is slidably mounted within the bore 120 of the hub. A thumb-screw 123 is mounted in the exterior of the hub, and has internal threads which ride on the external screw threads 124 provided on the hub. The traveler 122 includes a finger 125 which extends through longitudinal channel 126 into an annular groove on the inner surface of the thumbscrew 123 so that rotation of the thumbscrew and movement of the thumbscrew along the exterior of the hub causes the traveler to move with the thumbscrew. The traveler is secured to the pullwire 87 so that any movement of the traveler pushes or pulls the pullwire. When used in combination with the tear-away sheath illustrated in FIG. 25, for example, the rotation of the thumb screw is translated into gentle, smooth, controllable and even tension on the pullwire and loops 84, and clean tearing of the tear-away sheath along the line established by the starter notches 82 shown in FIG. 25. The hub assembly may be combined with any of the embodiments disclosed herein, or with any pull-wire structure disclosed in the prior art. It should be noted that reversal of the direction of turning of the thumb-screw will result in a distal movement of the traveler, so that the assembly may be used to push a push rod or wire.

The hub assembly 118 shown in FIG. 46 is assembled so as to connect the thumbscrew 123 to the pullwire 87, so that the pullwire may be pulled proximally. The traveler may be connected to the insertion catheter 2, as shown in FIG. 47, so that the thumbscrew operates on the insertion catheter. Note in FIG. 47 that the insertion catheter 2 extends proximally, and it is in contact with the traveler 122 and secured to the traveler. Thus the delivery catheter 2 may be advanced distally or withdrawn proximally by action of the thumbscrew. An additional traveler 127 and thumbscrew 128 are added to the hub assembly, engaging the pullwire 87 at a location proximal to the point of engagement of the overlying guide sheath. Three or more overlying sheaths may likewise be independently operated with travelers in similar manner.

FIG. 48 shows an alternative mechanism for pulling the stent sheath cords. The thumb roller 130 is connected to the finger via a small axle 131 (and a duplicate thumb-roller is on the opposite side of the axle), and the finger 125 is in turn connected to the traveler 122. The geared circumference 132 of the thumb roller tightly engages the rolling surface 133, either by providing a tight high friction fit or via a rack and pinion assembly with a geared surface on the surface of the thumb roller. The traveler 122 is connected to the longitudinally moving catheter component, whether it be the pull cords, everting sheath, zip-strips or other component. With this construction, the operator of the catheter may provide smooth pulling or pushing force on the longitudinal sliding member, and the friction lock provided by the tight fit will hold the component in place relative to other members of catheter assembly.

FIG. 49 shows another embodiment of a linear translator which uses a hand held electric motor. The translating rod 136 is threaded, and engages the threaded bore of traveler 137. The traveler is held within the hub in slidable but non-rotating manner by the runner 138, which moves in longitudinal channel 126 so that rotation of the translating rod forces longitudinal translation of the traveler. The translating rod is attached to electric motor 139 which may be operated in either direction to rotate the threaded translating rod and cause pulling or pushing force on the traveler. Movement of the traveler 137 causes corresponding movement of the pull wire 87 or push rod. The motor 139 may be a cordless motor having forward, reverse and lock positions, and may actually be comprised of a cordless screw driver or similar commercially available motor drive, with the translating rod having a hexagonal cross section to mate with the screw driver chuck. The motor handle is integral with the motor body, thus comprising an in-line motor drive. With this embodiment, the gross positioning of the distal tip of the catheter and the final deployment of the stent may be accomplished with one hand. Because the motor body is in-line with the catheter, it may be conveniently used as a handle for gross adjustment and fine adjustment of the catheter. Additional motor and translating screw assemblies may be coupled to the catheter sheath, or to both the catheter sheath and the pull wire, to permit motorized fine adjustment of these components. Foot switches may be used to operate one or more of the motors so that the operators hands are free to manipulate the catheter.

The linear translating mechanism shown in FIGS. 50 and 51 operate by applying hydraulic force to an actuator disposed within the distal end of the delivery catheter 2. This eliminates the need for a pullwire or other structure that must extend the entire length of the catheter, enabling construction of a more flexible catheter. As shown in FIGS. 50 and 51, the proximal hub assembly comprises a hydraulic actuator 140 including a chamber 141, a piston assembly including an input ram 142 and a hydraulic disk 143 connected to the handle 144 via the ram. The ram is threaded, and engages the threaded bore of the hydraulic chamber. Turning the handle drives the ram and disk into the chamber, and forces hydraulic fluid (most conveniently, saline solution) through the catheter lumen 145 and into distal hydraulic actuator 146. Distal hydraulic actuator has its own disk 147 and ram 148, which are forced to move as the distal hydraulic chamber 149 is filled with fluid. The distal ram may be the pull cord, strips, or wires used to tear the various embodiments of the stent retaining mechanism, or it may be small rod attached to the cords, strips or wires. The ram 148 slides through sealed opening in the distal chamber 149. The distal hydraulic chamber 146 may be reversed in orientation and placed proximally of the stent, as shown in FIG. 51, so that the pulling force may be applied from the proximal side. Also shown in FIG. 51 is the use of the syringe 150 which serves as the hydraulic chamber. The syringe plunger 142 is connected to the handle 144 through linkage 151.

It can readily be appreciated that the fluid supply and orientation of the distal actuator may be varied to cause pushing or pulling according to design preferences.

Figure 52:
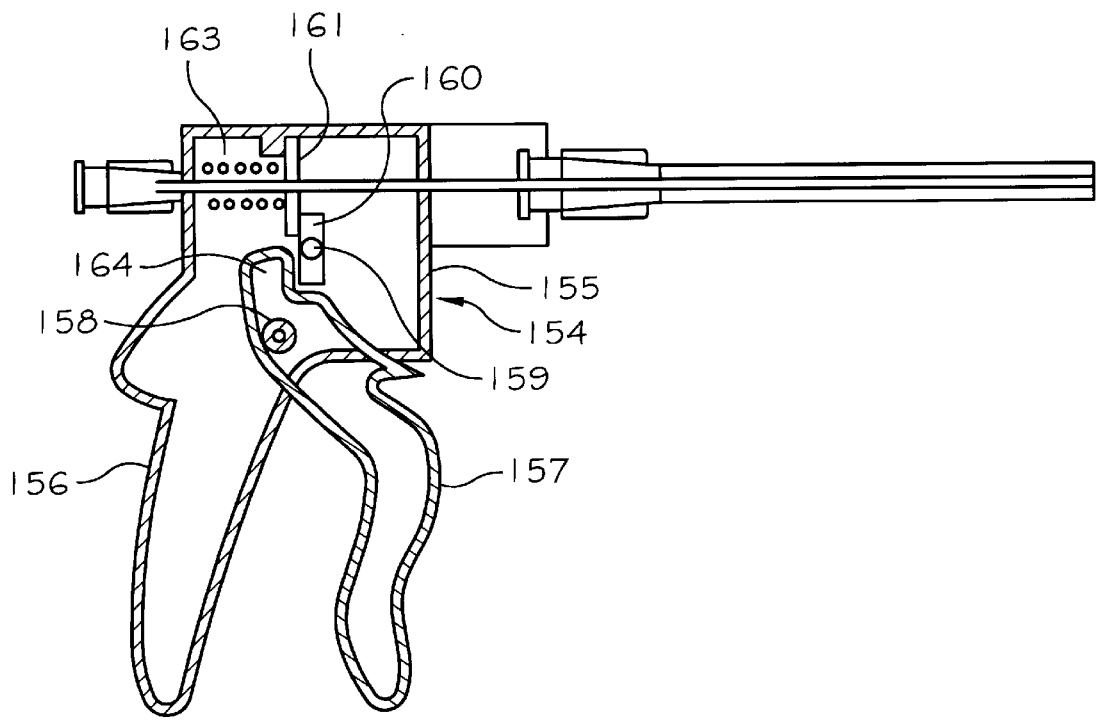
FIG. 52 shows a cross section of a gun assembly for use with the various catheters.

FIG. 52 shows an embodiment of a caulk gun-type linear translator, which comprises a gun assembly 154 including a frame 155, a grip 156, a trigger 157 mounted on a pivot 158, a reversing arm 159 mounted on a second pivot 160, friction engagement block 161 which engages translating rod 162, and a return spring 163 which acts to push the engagement block in the position shown. In FIG. 52, the pull cord is attached to the translating rod 162. Squeezing the trigger 157 causes the hammer 164 at the top of the trigger to push the bottom of the reversing arm forward, and thus the top of the reversing arm pushes the friction engagement block 161 rearward. The friction engagement block tilts slightly as it moves rearward, and engages the translating rod 162 with frictional force, and carries the translating rod with it. This rearward movement of the translating rod results in a pulling force on the pull wire and the tear strips, zip-strip, or pull cords attached to it. Reversal of the action, to create a pushing action, may be accomplished by removal of the reversing arm, in which case the trigger will act directly on the engagement block.

Figure 53:
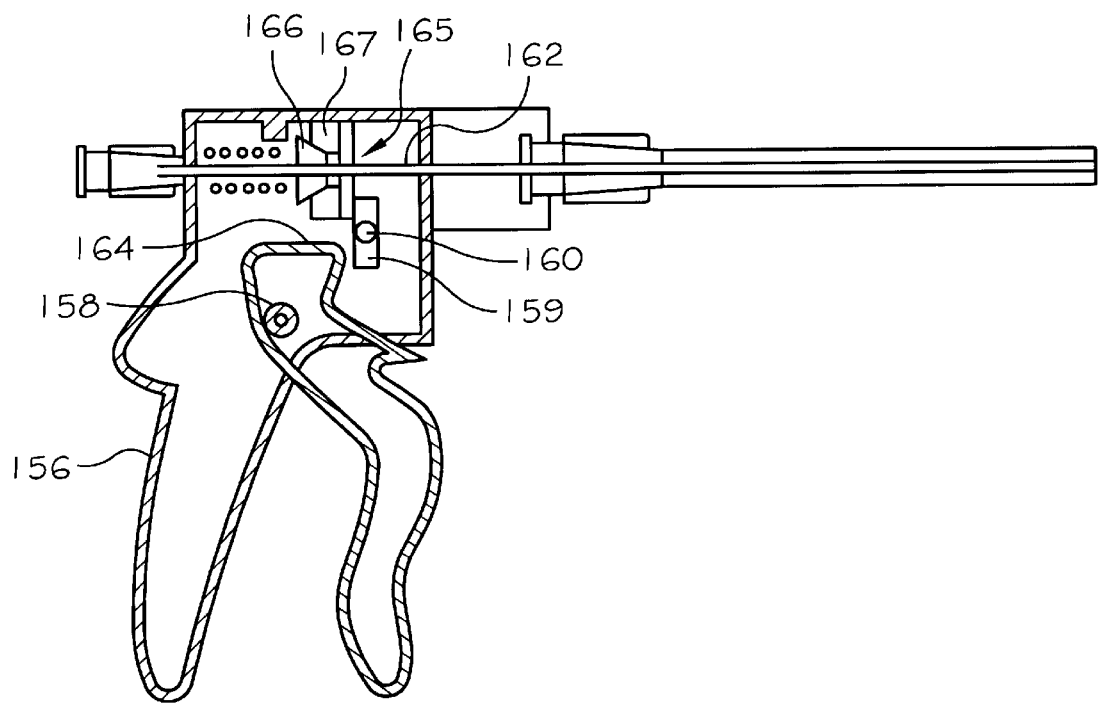
FIG. 53 shows a cross section of a gun assembly for use with the various catheters.

FIG. 53 includes many of the same parts as the gun of FIG. 52. The frictional engagement block is replaced by pinch mechanism 165. The pinch mechanism is a compressible frustoconical tube 166, and is surrounded by conical pusher 167 mounted on the top of the trigger 157 and opposed by return spring 163. As the conical pusher is forced rearward by the trigger action, it compresses the compressible tube, and causes the tube to grip the translating rod 162, so that the translating rod 162 is carried rearward with the compressible tube. After the stroke, the compressible tube is forced to its original position by the return spring.

Figure 54:
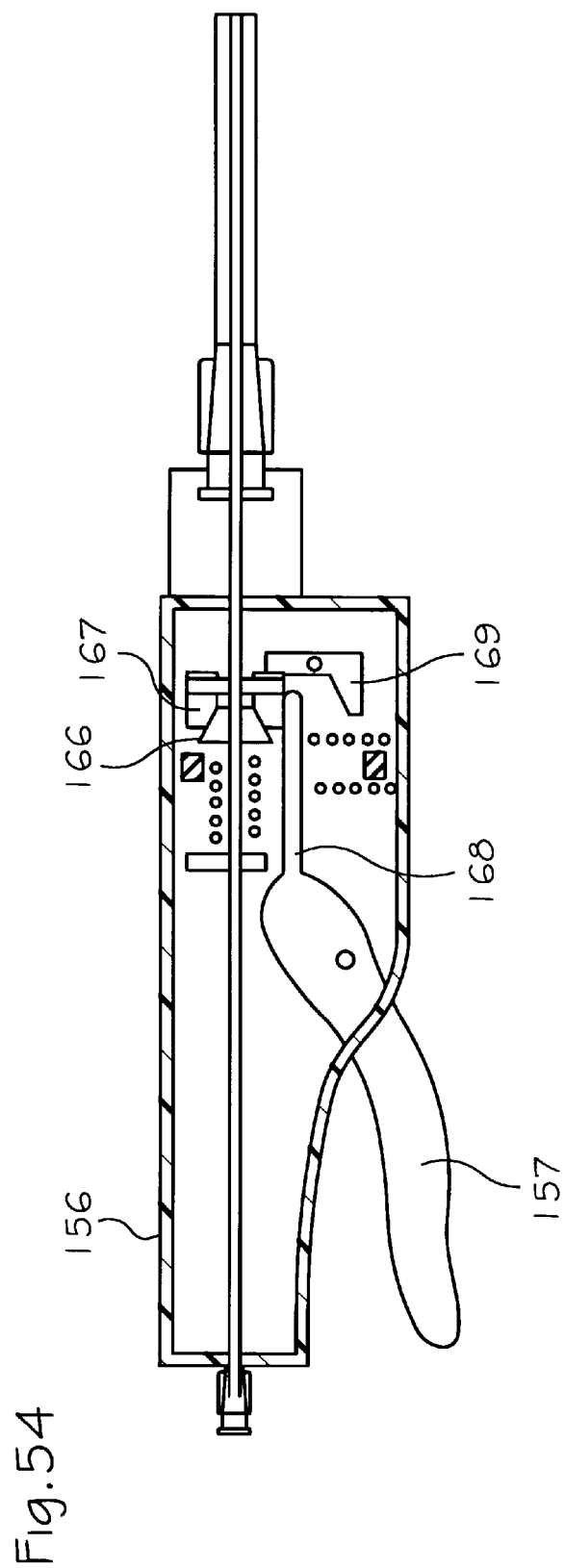
FIG. 54 shows a cross section of an in-line gun assembly for use with the various catheters

In FIG. 54, the gun drive mechanisms of FIGS. 52 and 53 are modified by moving the grip and trigger to an in-line position, meaning that the length of the trigger 157 is generally parallel to the long axis of the catheter itself. This allows the gun handle 156 to be used as a handle for the catheter itself, and permits easier operation of the trigger 157. The gun assembly is modified to permit in-line operation, principally by addition of the extension 168 which operably connects the trigger to the reversing arm 159. The reversing arm is modified by addition of a contact block 169 sized and dimensioned to obstruct the downward movement of the trigger extension 138.

Figure 55:
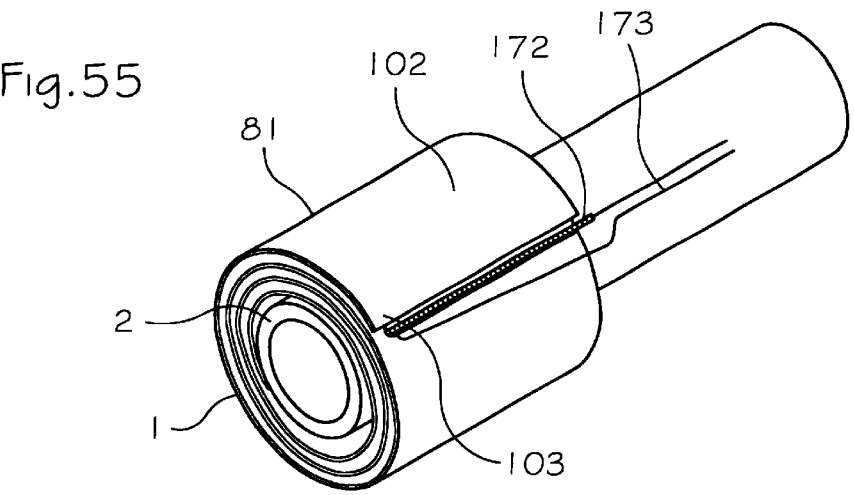
FIG. 55 shows a heat release mechanism for a self expanding stent.
Figure 56:
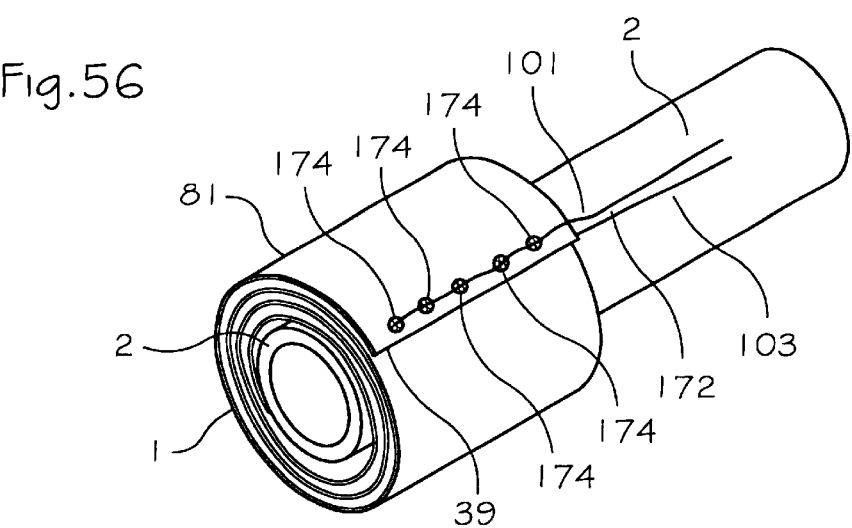
FIG. 56 shows a heat release mechanism for a self expanding stent.
Figure 57:
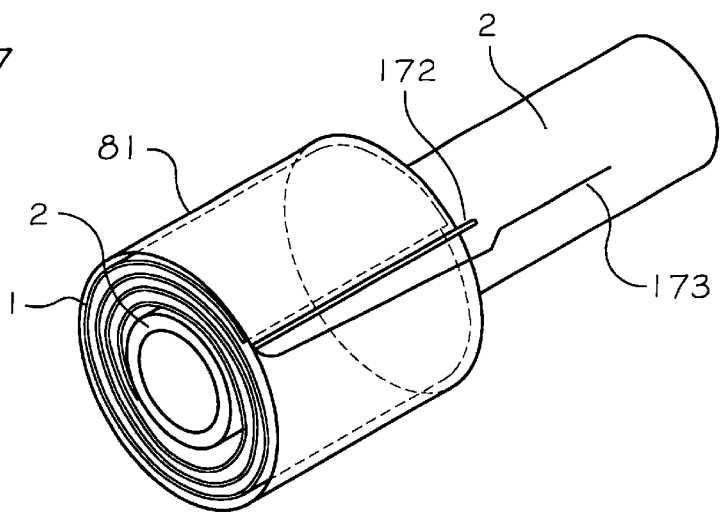
FIG. 57 shows a heat release mechanism for a self expanding stent.

FIGS. 55, 56 and 57 illustrate another embodiment of non-sliding release mechanisms for the self expanding stents. In each of these embodiments, the retaining structure is separated by melting under the heat of a nichrome wire. In FIG. 55, the self expanding stent is secured to the distal tip of catheter 2. A joining bead 171 joins the outer edge 39 of the stent 1 to the underlying layer, similar to the bead shown in FIG. 34. The bead is preferably made with an adherent or adhesive material with a low melting temperature, such as polyester. The heating wire (preferably nichrome) 172 is placed under the bead, and grounded through ground wire 173. When a small and safe current is passed through the nichrome wire, it heats up and melts the bead, thereby releasing the stent. FIG. 56 shows a similar construction, with the outer edge 39 of the stent 1 glued to the underlying layer with several plugs of adherent material placed in holes 174. Again, the plugs are made of with an adherent or adhesive material with a low melting temperature, such as polyester, so that passage of current through the heating wire melts the plugs, thereby releasing the stents. The plugs may extend through multiple layers or all layers of the stent, thus locking them together and serving as meltable locking pins, or they may extend only through the upper layer and serve an adhesive dabs to secure the outer layer to the underlying layer. In FIG. 57, the stent 1 is secured with the sheath 81, as illustrated in various embodiments above, and the heating wire 172 runs under the sheath, attached to the ground wire 173. Passage of electric current through the heating wire causes it to heat up sufficiently to melt the sheath in the vicinity of the wire, thereby melting a tear in the sheath and releasing the stent. In reference to FIGS. 55, 56 and 57, the sealing material used in each embodiment may be comprised of electrolytically dissolvable material and the electrical connections may be used to pass current through the material to cause the electrolytic dissolution of the material. Electrolytic materials useful in these embodiment include, for example stainless, bismuth, lead, etc. The area of desired electrolytic dissolution can be controlled by coating the stent with a polymer or biopolymer (PET, for example, perhaps impregnated with therapeutic agents) in all areas in which dissolution of the stent is not desired.

The overall structure of the stent insertion catheter has been described in various embodiments. Any structure commonly used in the prior art to insert devices into the blood vessels may be used, and any system may be used. There is some variation on the method of deployment of intraluminal devices, and all such variations may be employed in combination with the inventions described above. Basic access to the vasculature is expected to be accomplished percutaneously, using the Seldinger technique. This requires use of an insertion needle, followed by an insertion guide which is placed over the insertion needle, followed by a large insertion catheter which is inserted over the insertion guide. The insertion catheter extends only a few centimeters into the blood system, and serves to protect the insertion point from unnecessary damage from the several catheters which may be inserted in the course of a single operation. A guide catheter, discussed above in relation to the various embodiments, may then be inserted through the vasculature to a point near the diseases portion of the blood vessel. Placement of the guide catheter may be accomplished with the aid of a guide wire. With this guide catheter in place, the delivery catheter of the various embodiments may be inserted and steered to the diseased site. Thus it is desirable to use an insertion catheter that is steerable, and can be snaked, pushed and twisted through the intracranial vasculature. For many of the embodiments discussed above, the insertion catheter may be made of an 0.020 in. guidewire, or even smaller guidewires as they become available. Hollow guidewires can provide the supporting structure as well as the central lumen used for the pull wires used in the various embodiments, and have already proven capable of safe insertion into the vasculature. For the many embodiments described above which use sheaths, various sheaths are commercially available.

This specification has described several means for retaining, delivering and deploying stents inside the vasculature of the human brain. The inventions described above have been developed in the environment of intra-cranial stent placement. However, the benefits provided by the various embodiments may be employed in any environment, including intraluminal placement of a variety of implants, or operation of a variety of devices from remote locations. Although emphasis has been placed on description of the stent deployment mechanisms in combination with rolled sheet stents, these stent deployment mechanisms can be used to deliver and deploy any manner of stent. A large number of variations in implementation of the inventions may be expected. Catheter placement may be facilitated with the use of common guide catheters and guide wires. Expansion of the stent may be aided by a micro-balloon placed at the tip of the insertion catheter. Other features described, such as the materials of the stent, the arrangement, number and degree of openings or slats, and geometry of the release tab may be improved upon as experience with the devices and methods described above dictates. The various hub mechanisms and release mechanisms may be mixed and matched according to design preference. Thus, while the preferred embodiments of the devices and methods have been described, they are merely illustrative of the principles of the invention. Other embodiments and configurations may be devised without departing from the spirit of the inventions and the scope of the appended claims.

We claim:

1. A stent delivery system comprising:

an insertion catheter having a distal end and a proximal end;

a rolled stent mounted on the distal end of the insertion catheter, said rolled stent having a small diameter configuration and a large diameter configuration;

said rolled stent having an outer edge overlapping an outer surface of an outer layer;

binding means for affixing the outer edge to the outer surface of the outer layer of said rolled stent, wherein the binding means forms a sealed roll of the rolled stent when the rolled stent is in its small diameter configuration; and release means for releasing the sealed roll to allow the rolled stent to expand to its large diameter configuration;

wherein the binding means comprises tape securing the outer edge to the outer surface of the outer layer of said rolled stent.

2. A stent delivery system comprising:

an insertion catheter having a distal end and a proximal end;

a rolled stent mounted on the distal end of the insertion catheter, said rolled stent having a small diameter configuration and a large diameter configuration;

said rolled stent having an outer edge overlapping an outer surface of an outer layer;

binding means for affixing the outer edge to the outer surface of the outer layer of said rolled stent, wherein the binding means forms a sealed roll of the rolled stent when the rolled stent is in its small diameter configuration; and release means for releasing the sealed roll to allow the rolled stent to expand to its large diameter configuration;

wherein the binding means comprises a weld securing the outer edge to the outer surface of the outer layer of said rolled stent.

3. A stent delivery system comprising:

an insertion catheter having a distal end and a proximal end;

a rolled stent mounted on the distal end of the insertion catheter, said rolled stent having a small diameter configuration and a large diameter configuration;

said rolled stent having an outer edge overlapping an outer surface of an outer layer;

wherein the outer edge is secured to the outer surface of the outer layer of said rolled stent thus forming a sealed roll when the rolled stent is in its small diameter configuration;

at least one pre-scored line scored into the outer layer; and;

a zip-strip disposed under the outer layer of the rolled stent along the scoring line, and a pull-strip attached to the zip-strip, said pull-strip being operable from the proximal end of the insertion catheter to tear the outer layer along the pre-scored line.

* * * * *